(12) United States Patent
Nick et al.

(10) Patent No.: US 8,753,662 B2
(45) Date of Patent: Jun. 17, 2014

(54) METHODS AND COMPOSITIONS FOR THE DISRUPTION OF BIOFILMS

(75) Inventors: Jerry A. Nick, Denver, CO (US); Quinn M. Parks, Denver, CO (US)

(73) Assignee: National Jewish Health, Denver, CO (US)

(*) Notice: Subject to any disclaimer, the term of this patent is extended or adjusted under 35 U.S.C. 154(b) by 1095 days.

(21) Appl. No.: 12/031,029

(22) Filed: Feb. 14, 2008

(65) Prior Publication Data
US 2008/0199509 A1    Aug. 21, 2008

Related U.S. Application Data

(60) Provisional application No. 60/890,168, filed on Feb. 15, 2007.

(51) Int. Cl.
*A61K 9/00*    (2006.01)

(52) U.S. Cl.
USPC ............... 424/423; 514/2; 514/12; 514/44

(58) Field of Classification Search
None
See application file for complete search history.

(56) References Cited

U.S. PATENT DOCUMENTS

| | | | |
|---|---|---|---|
| 5,260,224 A | 11/1993 | Stossel et al. | |
| 5,312,813 A | 5/1994 | Costerton et al. | |
| 5,462,644 A | 10/1995 | Woodson | |
| 5,464,817 A | 11/1995 | Stossel et al. | |
| 5,981,568 A | 11/1999 | Kunz et al. | |
| 6,143,037 A | 11/2000 | Goldstein et al. | |
| 6,586,425 B2 | 7/2003 | Kaufman et al. | |
| 7,144,992 B2 | 12/2006 | Madhyastha | |
| 2002/0099438 A1 | 7/2002 | Furst | |
| 2003/0113742 A1 | 6/2003 | Whiteley et al. | |
| 2005/0233950 A1* | 10/2005 | Madhyastha | 514/8 |
| 2006/0002889 A1 | 1/2006 | Fitzpatrick | |
| 2006/0030539 A1* | 2/2006 | Nick et al. | 514/44 |
| 2006/0239940 A1 | 10/2006 | Nakayama et al. | |
| 2007/0003538 A1 | 1/2007 | Madhyastha | |

FOREIGN PATENT DOCUMENTS

| | | |
|---|---|---|
| WO | WO 02/083167 | 10/2002 |
| WO | WO 03/088914 | 10/2003 |
| WO | WO 2005/094579 | 10/2005 |

OTHER PUBLICATIONS

Jesaitis et al ("Compromised Host Defense on *Pseudomonas aeruginosa* Biofilms," Characterization of Neutrophil and Biofilm Interactions, Journal of Immunology 2003, 171: 4329-4339 )[.*
Tang et al ("Anionic poly(amino acid)s dissolve F-actin and DNA bundles, enhance DNase activity, and reduce the viscosity of cystic fibrosis sputum," Am J Physiol Lung Cell Mol Physio 1289: L599-L605, 2005).*

International Preliminary Report on Patentability for International (PCT) Patent Application No. PCT/US08/53970, Issued Aug. 19, 2009.
U.S. Appl. No. 12/115,880, Aug. 28, 2008, Nick, et al.
Balfour-Lynn, "The protease-antiprotease battle in the cystic fibrosis lung", Journal of the Royal Society of Medicine, 1999, vol. 92, No. 37 Supplement, pp. 23-30.
Barnett, "The rationale for the daily use of an antimicrobial mouthrinse", JADA, Nov. 2006, vol. 137, pp. 16S-21S.
Bleazard, "The Role of Oxygen and the Interaction of Human Neutrophils with Viable Planktonic and Biofilm *Pseudomonas aeruginosa*" Montana State University, available at http://vvww.erc.montana.edu/Res-Lib99-SW/pubs/Theses/2001/Thesis01_Bleazard.htm., Jul. 2001, pp. 1-2.
Boucher, "An Overview of the Pathogens of Cystic Fibrosis Lung Disease", Advanced Drug Delivery Reviews, 2002, vol. 54, pp. 1359-1371.
Camenzind, et al., "Local Vascular Therapy Against Thrombus and Proliferation: Clinical Trials Update", American College of Cardiology, 47th Annual Scientific Session, available at www.medscape.com/viewarticle/428985, printed Apr. 26, 2007, pp. 1-3.
Donlan, "Biofilms and Device-Associated Infections", Emerging Infectious Diseases, Mar.-Apr. 2001, vol. 7, No. 2, pp. 277-281.
Egerbacher et al., "Ciprofloxacin causes cytoskeletal changes and detachment of hauman and rat chodrocytes in vitro", Archives of Toxicology, 2000, vol. 73, pp. 557-563.
Gong et al., "Salivary Film Expresses a Complex Macromolecular Binding Site for *Streptococcus sanguis*", The Journal of Biological Chemistry, Mar. 24, 2000, vol. 275, No. 12, pp. 8970-8974.
Halmerbauer, et al., "The relationship of eosinophil granule proteins to ions in the sputum of patients with cystic fibrosis", Clinical and Experimental Allergy, 2000, vol. 30, pp. 1771-1776.
Hagemann, "Cystic Fibrosis Drug Therapy", Journal of Pediatric Health Care, May/Jun. 1996, vol. 10, pp. 127-134.
Jackson, et al., "The Role of Biofilms in Airway Disease", Seminars in Respiratory and Critical Care Medicine, 2003, vol. 24. No. 6, pp. 663-670.
Jaffé, et al., "Anti-Inflammatory Effects of Macrolides in Lung Disease." Pediatric Pulmonary, 2001, vol. 31, pp. 464-473.
Konstan et al., "Effect of High-Dose Ibuprofen in Patients with Cystic Fibrosis", The New England Journal of Medicine, Mar. 30, 1995, vol. 332, pp. 848-854.
Lethem, et al., "The Origin of DNA Associated With Mucus Glycoproteins in Cystic Fibrosis Sputum." The European Respiratory Journal : Official Journal of the European Society for Clinical Respiratory Physiology 1990, vol. 3, pp. 19-23.
Olsson, et al., "Arginie-Rich Cationic Proteins of Human Eosinophil Granules", Laboratory Investigation; A Journal of Technical Methods and Pathology, 1977, vol. 36, No. 5, pp. 493-500.
Perks, et al., "DNA and Actin Bind and Inhibit Interleukin-8 Function in Cystic Fibrosis Sputa", American Journal of Respiratory and Critical Care Medicine, 2000, vol. 162, pp. 1767-1772.

(Continued)

*Primary Examiner* — Suzanne Ziska
(74) *Attorney, Agent, or Firm* — Sheridan Ross P.C.

(57) ABSTRACT

The invention relates to methods of inhibiting biofilm formation or reducing biofilms in a subject or on a device or surface by administering a charged compound such as a polyamino acid to a subject, device or surface. The invention also relates to compositions for inhibiting biofilm formation or reducing biofilms.

19 Claims, 32 Drawing Sheets

(56) References Cited

OTHER PUBLICATIONS

Rowe, et al., "Mechanisms of Disease: Cystic Fibrosis", The New England Journal of Medicine, May 12, 2005, vol. 352, pp. 1992-2001.

Schwab, et al., "Role of Actin Filament Network in Burkholderia Multivorans Invasion in Well-Differentiated Human Airway Epithelia." Infection and Imunity, Nov. 2003, vol. 71, No. 11, pp. 6607-6609.

Sheils, et al., "Actin Filaments Mediate DNA Fiber Formation in Chronic Inflammatory Airway Disease." American Journal of Pathology, Mar. 1996, vol. 148, No. 3, pp. 919-927.

Stossel, "Gesolin: Another Potential Therapy for CF Sputum", available at http://www.cfri.org/news/94fa11/res394f.html, Fall 1994, pp. 1-2.

Tamaoki, "The Effects of Macrolides on Inflammatory Cells", Chest Journal, 2004, vol. 125, No. 2, pp. 41S-51S.

Tang, et al., "Anionic poly (amino acid)s dissolve F-actin and DNA bundles, enhance Dnase activity, and reduce the viscosity of cystic fibrosis sputum", American Journal of Physiology-Lung Cellular and Molecular Physiology, Jun. 17, 2005, vol. 289, pp. 599-605.

U.S. Preventive Services Task Force, "Aspirin for the Primary Prevention of Cardiovascular Events: Recommendation and Rationale", Annals of Internal Medicine, Jan. 15, 2002, vol. 136, No. 2, pp. 157-160.

Udagawa, et al., Cytochalasin E, an epoxide containing Aspergillus-derived fungal metabolite, inhibits angiogenThe Journal of Pharmacology and Experimental Therapeutics, 2000, vol. 294, No. 2, pp. 421-427.

Vasconcellos, et al., "Reduction in Viscosity of Cystic Fibrosis Sputum in Vitro by Gelsolin", Science, Feb. 18, 1994, vol. 263, No. 5149, pp. 964-971.

Weiner, et al., "The Antimicrobial Activity of the Cathelicidin LL37 is Inhibited by F-actin Bundles and Restored by Gelsolin." Am. J Respir. Cell Mol. Biol., 2003, vol. 28, pp. 738-745.

Zahm, et al., "Improved Activity of an Actin-Resistant DNase I Variant on the Cystic Fibrosis Airway Secretions" Am J Respir Crit Care Med., 2001, vol. 163, pp. 1153-1157.

HØiby, "Understanding bacterial biofilms in patients with cystic fibrosis: current and innovative approaches to potential therapies", Journal of Cystic Fibrosis, 2002, vol. 1, pp. 249-254.

Jansen, et al., "Prevention of biofilm formation by polymer modification", Journal of Industrial Microbiology, Oct. 1995, vol. 15, No. 4, pp. 391-396.

Jesaitis, et al., "Compromised Host Defense on *Pseudomona aeruginosa* Biofilms: Characterization of Neutrophil and Biofilm Interactions", The Journal of Immunology, 2003, vol. 171, pp. 4329-4339.

Kubanek, et al., "Seaweed resistance to microbial attack: a targeted chemical defense against marine fungi", PNAS, Jun. 10, 2003, vol. 100, No. 13, pp. 6916-6921.

Walker et al., "Enhanced *Pseudomonas aeruginosa* biofilm development mediated by human neutrophils", Infection and Immunity, Jun. 2005, vol. 73, No. 6, pp. 3963-3701.

Schultz, "Macrolide activities beyond their antimicrobial effects: macrolides in diffues panbronchiolitis and cystic fibrosis", Journal of Antimicrobial Chemotherapy, 2004, vol. 54, No. 1, pp. 21-28.

Yasuda, "Interaction between Biofilms Formed by *Pseudomonas aeruginosa* and Clarithromycin", Antimicrobial Agents and Chemotherapy, Sep. 1993, vol. 37, No. 9, pp. 1749-1755.

International Search Report for International (PCT) Patent Application No. PCT/US08/53970, mailed Sep. 16, 2008.

Written Opinion for International (PCT) Patent Application No. PCT/US08/53970, mailed Sep. 16, 2008.

Clark, "The Commonality of Cutaneous Wound Repair and Lung Injury," 1991, Chest. 99:57S-60S.

Cooper, "Effects of Cytochalasin and Phalloidin on Actin", J. Cell Biol. 105:1473-78 (1987).

Khardori et al., "Biofilms in Device-related infections," J of Industrial Micro. 15:141-147, 1995.

Parks et al., "Neutrophil enhancement of *Pseudomonas aeruginosa* biofilm development", J. Med. Microbiol. 58:492-502 (2009).

Smith et al., "Action of Cytochalasin B on Cultured Human Lymphocytes" Nature 16(216):1134-35 (1967).

Spooner et al., "Effects of Cytochalasin B upon Microfilaments Involved in Morphogenesis of Salivary Epithelium", Proc. Natl. Acad. Sci. USA 66(2):360-61 (1970).

Van Gameren et al., "Early complications of stenting in patients with congenital heart disease: a multicentre study," European Heart Journal (2006) 27, 2709-2715.

Jensen et al. "Colistin inhalation therapy in cystic fibrosis patients with chronic *Pseudomonas aeruginosa* lung infection," Journal of Antimicrobial Chemotherapy, Jan. 1987, vol. 19, No. 6, pp. 831-838.

Musk et al. "Chemical Countermeasures for the Control of Bacterial Biofilms: Effective Compounds and Promising Targets," Current Medicinal Chemistry, Aug. 1, 2006, vol. 13, No. 18, pp. 2163-2177.

Singh et al. "A component of innate immunity prevents bacterial biofilm development," Nature, May 30, 2002, vol. 417, No. 6888, pp. 552-555.

Smith et al., "Action of Cytochalasin B on Cultured Human Lymphocytes" Nature, Dec. 1967, vol. 16, No. 216, pp. 1134-1135.

Takeoka et al. "The In Vitro Effect of Macrolides on the Interaction of Human Polymorphonuclear Leukocytes With *Pseudomonas aeruginosa* in Biofilm," Chemotherapy, Jan. 1, 1998, vol. 44, No. 3, pp. 190-197.

Yoon et al. "*Pseudomonas aeruginosa* Anaerobic, Respiration in Biofilms: Relationships to Cystic Fibrosis Pathogenesis," Developmental Cell, Oct. 1, 2002, vol. 3, pp. 593-603.

Zhang et al. "Antimicrobial peptide therapeutics for cystic fibrosis," Antimicrobial Agents and Chemotherapy, Jul. 1, 2005, vol. 49, No. 7, pp. 2921-2927.

Extended Search Report for European Patent Application No. 08729868.3, dated Oct. 30, 2012 11 pages.

\* cited by examiner

METHODS AND COMPOSITIONS FOR THE DISRUPTION OF BIOFILMS

CROSS-REFERENCE TO RELATED APPLICATIONS

This application claims the benefit of priority under 35 U.S.C. §119(e) from U.S. Provisional Application No. 60/890,168, filed Feb. 15, 2007, the entire disclosure of which is incorporated herein by reference for all purposes.

BACKGROUND OF THE INVENTION

Cystic fibrosis (CF) lung disease features persistent neutrophil accumulation to the airways from the time of infancy (1). In the absence of detectable infection or endotoxin, bronchioalveolar lavage studies have recovered neutrophils ranging from $10^5$ to $10^7$ per mL from the airways of CF children (1-3). These children are frequently exposed to environmental strains of P. aeruginosa, but early infections can be transient, or be eradicated by aggressive antibiotic treatment and an exuberant host defense (4-6). Initial success in eradicating P. aeruginosa acquired from environmental sources likely occurs due to a low density of organisms, a lack of antibiotic resistance, and a generally nonmucoid phenotype. Eventually, persistent P. aeruginosa infection appears inevitable and, by adulthood, 80% of CF patients are chronically infected.

Factors that allow P. aeruginosa to become persistent are of particular interest, as chronic P. aeruginosa infection is associated with increased morbidity and mortality in CF patients (7-9). The persistent P. aeruginosa infection is associated with numerous phenotypic and genetic changes by the bacteria within the CF airway, including the formation of biofilms (10-14). Bacterial biofilms are surface-attached communities of cells encased within a self-produced extracellular polysaccharide matrix independent of, but related to, mucoidy. Biofilm development proceeds through a series of programmed steps including initial surface attachment, formation of three-dimensional microcolonies, and finally the development of a 'mature' biofilm (15). The detection of a specific pattern of quorum-sensing signaling molecules in the CF airway suggests that P. aeruginosa in the CF airway exists primarily in the biofilm form (14), a conclusion supported by the inability of antibiotics and host defense mechanisms to eradicate the infection (10, 13, 14).

One of the predominant features of the CF airway is the chronic high-level influx of immune cells. Persistent neutrophil accumulation and necrosis in the CF airways results in sputum highly enriched with DNA, actin, and granule proteins, which are all implicated in the pathogenesis of CF lung disease (1, 16-20). A primary problem of *Pseudomonas* infection of the cystic fibrosis airway is the longevity of the infection. This infection, which can span decades, persists due to the formation of biofilms, a process facilitated by the presence of neutrophils and neutrophil-derived DNA and F-actin (22).

In addition to CF, a variety of other medical conditions and treatments can cause the undesirable development of biofilms. For example, a variety of microbial infections can be characterized by biofilm formation, including, but not limited to, infectious kidney stones, cystitis, catheter-related infection (kidney, vascular, peritoneal), medical device-related infections, prostatitis, dental caries, chronic otitis media, bronchiectasis, bacterial endocarditis, Legionnaire's disease, orthopedic implant infection, osteomyelitis, wounds, acne, and biliary stents. Therefore, there is a need in the art for improved therapeutic approaches for the inhibition of biofilm formation and/or the reduction or elimination of biofilms, which will be useful for the treatment of conditions such as cystic fibrosis, as well as other diseases and conditions that are associated with the formation of microbial biofilms.

SUMMARY OF THE INVENTION

One aspect of the invention relates to a method of inhibiting biofilm formation or reducing biofilms in a subject comprising administering to a subject a charged compound.

In some embodiments, the charged compound is a polyamino acid.

In some embodiments, the polyamino acid comprises both charged and neutral amino acids.

In some embodiments, the polyamino acid is anionic.

In some embodiments, the polyamino acid is polyaspartic acid or polyglutamic acid.

In some embodiments, the polyamino acid is cationic.

In some embodiments, the polyamino acid is polyarginine, polylysine or polyhistidine.

In some embodiments, the polyamino acid is between 50 and 300 amino acids in length.

In some embodiments, the method further comprises administering to the subject a protease inhibitor or an anti-DNA compound or an anti-mucin compound.

In some embodiments, the method further comprises administering to a subject a compound that inhibits accumulation of, inhibits necrosis of, or inhibits release of the cellular contents of, cells that undergo necrosis, at or proximal to the site of biofilm formation or the site of infection by a microorganism that forms biofilms.

In some embodiments, the cells that undergo necrosis are neutrophils.

In some embodiments, the compound inhibits the adherence of, migration to, or the sensing or response to chemoattractants by neutrophils, or inhibits the activity or release of a cytokine, chemokine or chemoattractant that attracts or enhances neutrophil activity.

In some embodiments, the compound is an anti-inflammatory compound.

In some embodiments, the method further comprises administering to the subject a compound for treatment of a disease or condition associated with biofilm formation.

In some embodiments, the compound is administered when a disease or condition associated with biofilm formation is diagnosed or suspected.

In some embodiments, the compound is administered prior to the treatment of the subject with a process that may cause a biofilm to form in the patient.

In some embodiments, the compound is administered with a pharmaceutically acceptable carrier.

In some embodiments, the compound is administered directly to or proximal to the site of biofilm formation or potential therefore.

In some embodiments, the compound is administered to the lung or airways of the subject.

In some embodiments, the compound is applied to a prosthetic graft that is subsequently administered to the patient, or the compound is administered to the subject receiving the graft prior to or during the implantation or utilization of the graft.

In some embodiments, the compound is applied to a catheter prior to or during use of the catheter by a subject.

In some embodiments, the compound is applied to the site of a wound or to the wound dressing when the wound is treated.

In some embodiments, the compound is applied to a medical device that subsequently contacts a subject tissue surface, wherein the compound is applied to the medical device prior to or during use of the medical device by a subject.

In some embodiments, the biofilm forms in connection with a disease or condition in an organ, tissue or body system.

In some embodiments, the biofilm forms on a surface of a tissue, organ or bodily part.

In some embodiments, the biofilm forms in connection with a disease or condition selected from the group consisting of: infectious kidney stones, cystitis, catheter-related infection (kidney, vascular, peritoneal), medical device-related infections, prostatitis, dental caries, chronic otitis media, cystic fibrosis, bronchiectasis, bacterial endocarditis, Legionnaire's disease, orthopedic implant infection, osteomyelitis, wounds, acne, and biliary stents.

In some embodiments, the subject has or is suspected of having cystic fibrosis.

In some embodiments, the microorganism is *Pseudomonas aeruginosa*.

An additional aspect of the invention relates to a composition for inhibiting biofilm formation or reducing biofilms in a subject, comprising a polyamino acid and a carrier suitable for application to the site of biofilm formation.

An additional aspect of the invention relates to a method of inhibiting biofilm formation or reducing biofilms on a device or surface comprising administering a charged compound to a device or surface that comprises a biofilm or on which a biofilm may form.

In some embodiments, the device or surface is a medical device such as a catheter.

In some embodiments, the device or surface is a contact lens.

In some embodiments, the contact lens is disposable.

In some embodiments, the device or surface is a pipe, item of manufacturing machinery or an item of food and beverage equipment.

In some embodiments, the charged compound is a synthetic polymer, a polynucleotide, or a peptide nucleic acid.

In some embodiments, the charged compound is administered to the subject prior to the development of the biofilm.

An additional aspect of the invention relates to a method of treating or preventing cystic fibrosis, bacterial keratitis or an infection associated with a severe burn or wound in a subject comprising administering to a subject a charged compound.

An additional aspect of the invention relates to a method of treating or preventing bacterial keratitis in a subject comprising administering to a subject a charged compound or treating a contact lens with a charged compound.

Lanes for A-C: 1. Ladder, 2. PAO1, 3. Early strain, 4. Late strain, 5. Negative control, 6. PAO1, 7. Early strain, 8. Late strain.

Lanes for D: 1. PAO1, 2. Early, 3. Late, 4. Negative control, 5. Ladder.

FIG. 2. *P. aeruginosa* biofilm formation is enhanced by human neutrophils. Biofilms were quantitated by crystal violet staining at 24 hours of bacterial growth in the presence (black bar) or absence (white bar) of neutrophils. At time 0, a fixed concentration of neutrophils ($2.5 \times 10^6$) was combined with *P. aeruginosa* at a 1:1 ratio, and decreasing 10 fold concentrations of bacteria to 1:1000. Strains examined were the lab standard PAO1 (A), a clinical strain isolated weeks after initial infection (B) and an isogenic strain isolated from the same patient four years later (C). Biofilm formation is presented on a log 10 scale, significance (*) was calculated by students T-test at $P<0.05$ with the comparison as noted. Fold change was obtained by averaging the raw readings per strain and concentration ratio. Background values were subtracted and *P. aeruginosa*+neutrophils average readings were divided by *P. aeruginosa* average readings. (D) is the fold change of (A), (E) is the fold change of (B), and (F) is the fold change of (C). *$P<0.001$ with the comparison as noted by one way ANOVA followed by Tukey's post test.

Figure 3A:
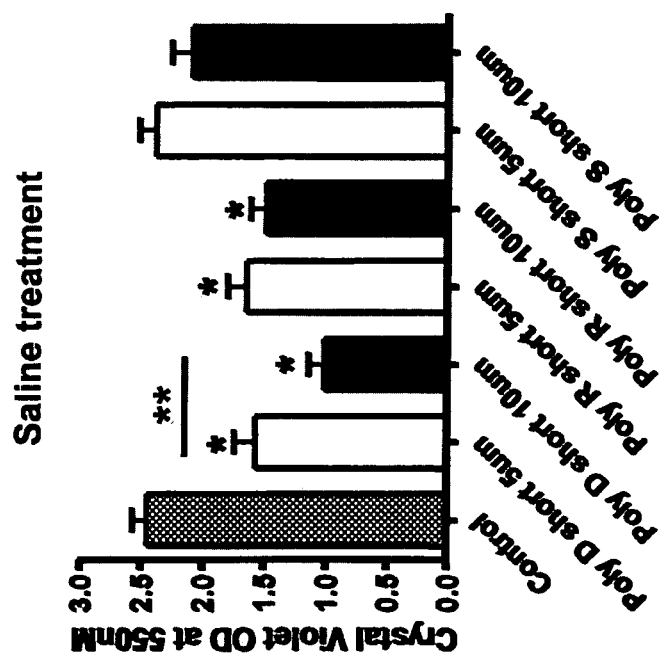

FIG. 3A. *Pseudomonas* PAO1 biofilms induced by neutrophils are sensitive to charged amino acid chains.

Figure 3B:
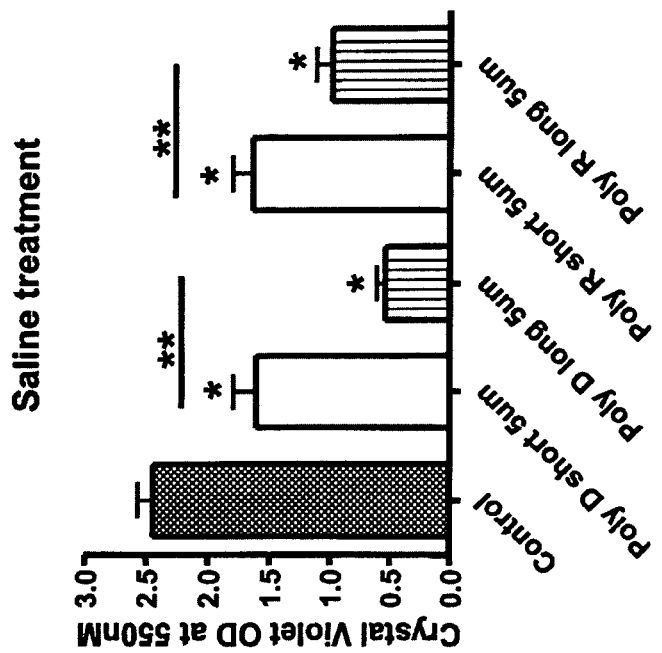

FIG. 3B. *Pseudomonas* PAO1 biofilms induced by neutrophils are sensitive to charged amino acid chains of different lengths.

Figure 3C:
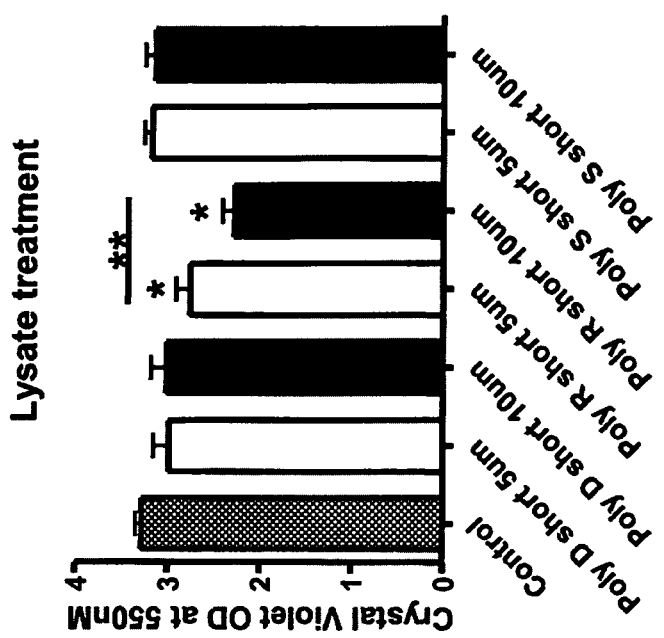

FIG. 3C. *Pseudomonas* PAO1 biofilms induced by neutrophils are sensitive to charged amino acid chains without the removal of the neutrophils present during biofilm formation.

Figure 3D:
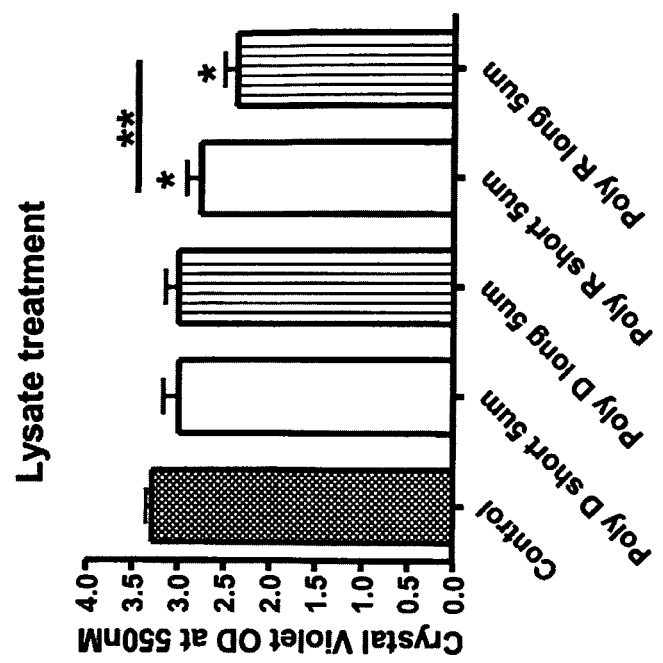

FIG. 3D. *Pseudomonas* PAO1 biofilms induced by neutrophils are sensitive to charged amino acid chains of different lengths without the removal of the neutrophils present during biofilm formation.

Figure 4A:
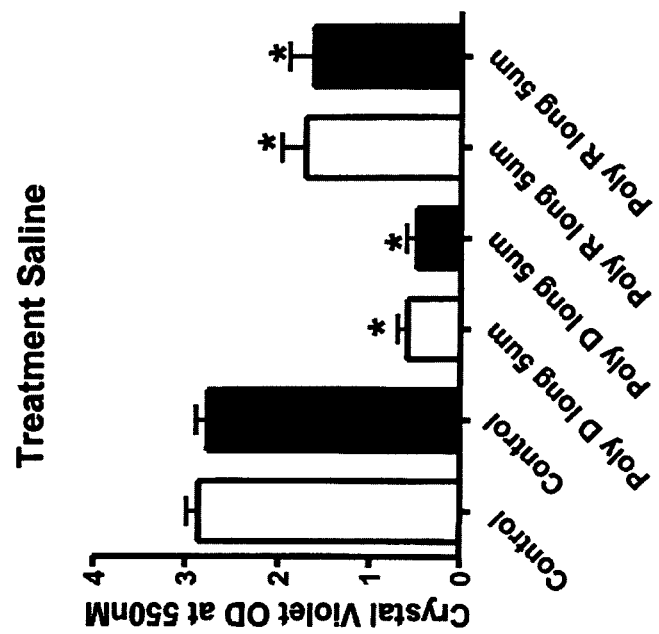

FIG. 4A. The effect of protease inhibitors on polyamino acid disruption of neutrophil induced *P. aeruginosa* biofilms.

Figure 4B:
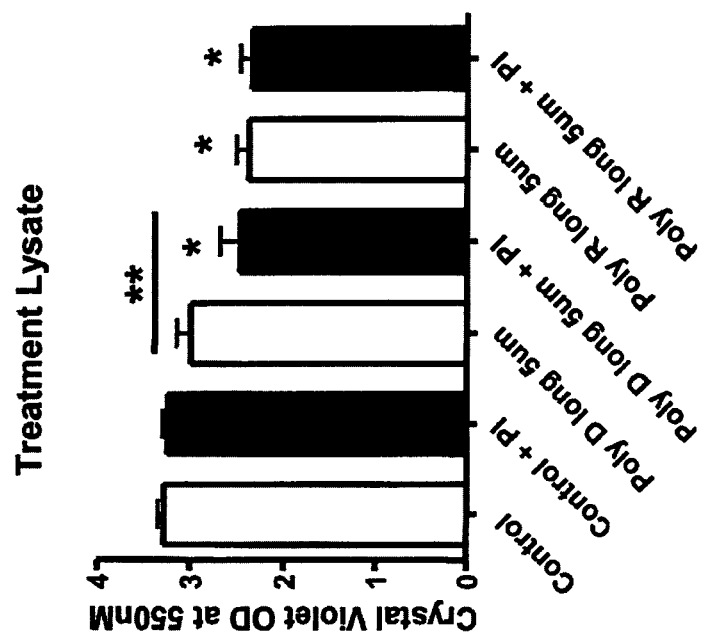

FIG. 4B. The effect of protease inhibitors on polyamino acid disruption of neutrophil induced *P. aeruginosa* biofilms without the removal of the neutrophils present during biofilm formation.

Figure 5:
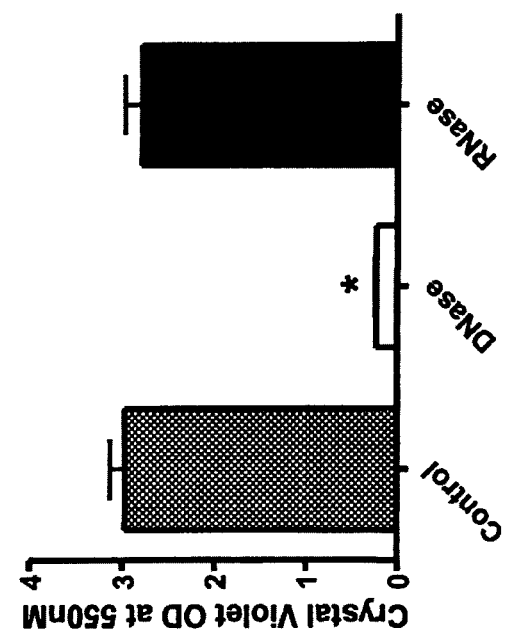

FIG. 5. Neutrophil-induced *P. aeruginosa* biofilms are disrupted by DNase.

Figure 6:
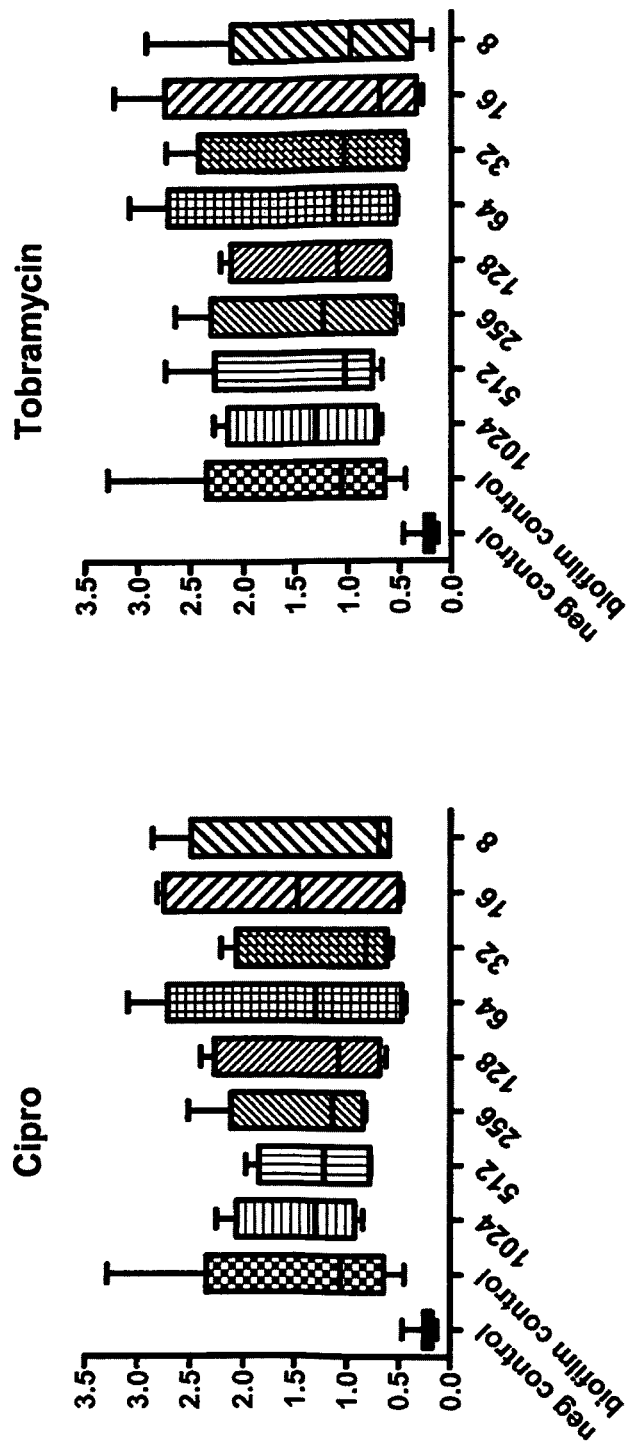

FIG. 6. Clinical levels of antibiotics alone do not disrupt biofilms.

Figure 7:
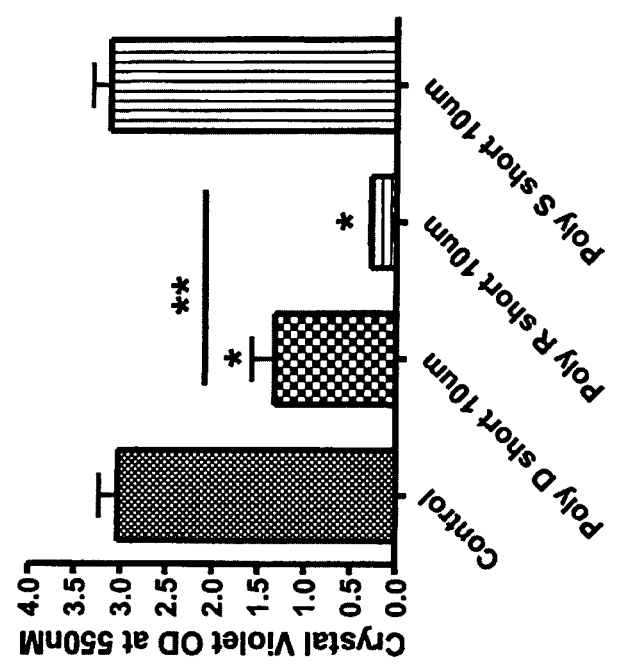

FIG. 7. The effect of charged amino acid chains in preventing neutrophil-induced enhancement of *P. aeruginosa* biofilms.

Figure 8:
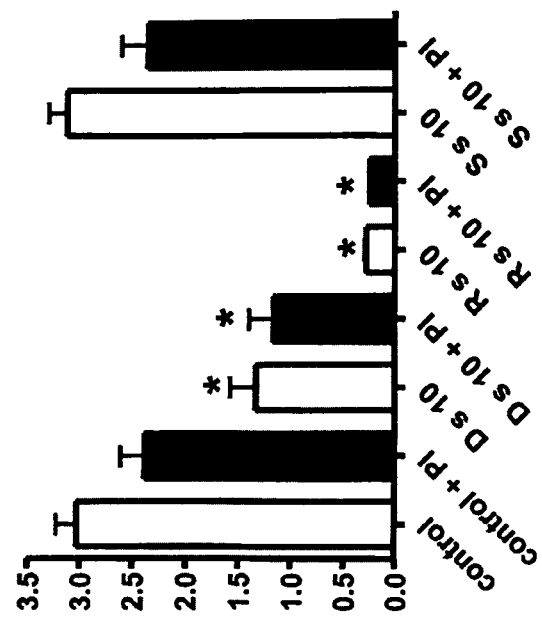

FIG. 8. The effect of protease inhibitors in combination with charged amino acid chains in preventing neutrophil-induced enhancement of *P. aeruginosa* biofilms.

Figure 9:
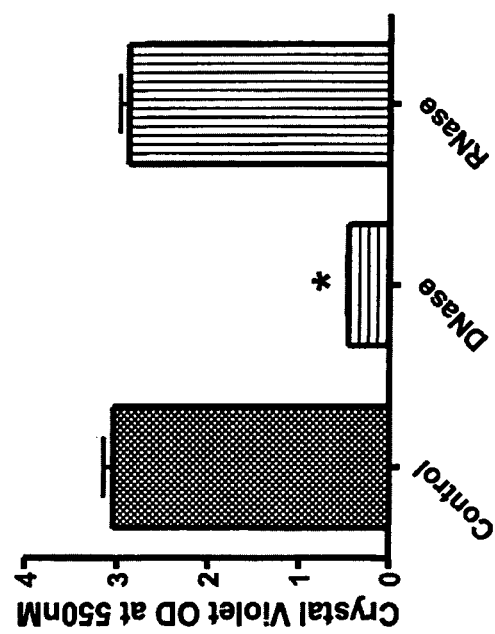

FIG. 9. Neutrophil-induced *P. aeruginosa* biofilm formation is prevented by DNase.

Figure 10:
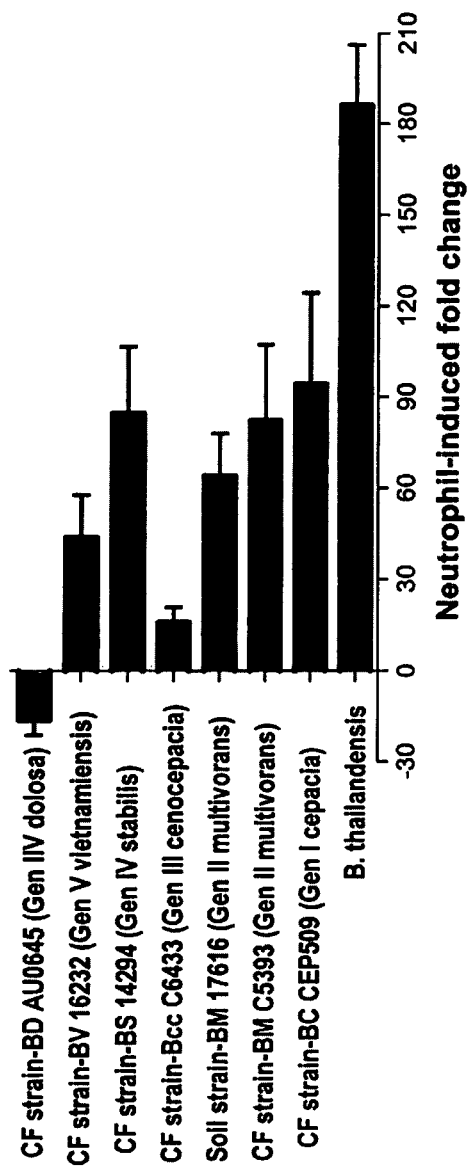

FIG. 10. Neutrophils significantly enhance early *Burkholderia* biofilm development.

Figure 11:
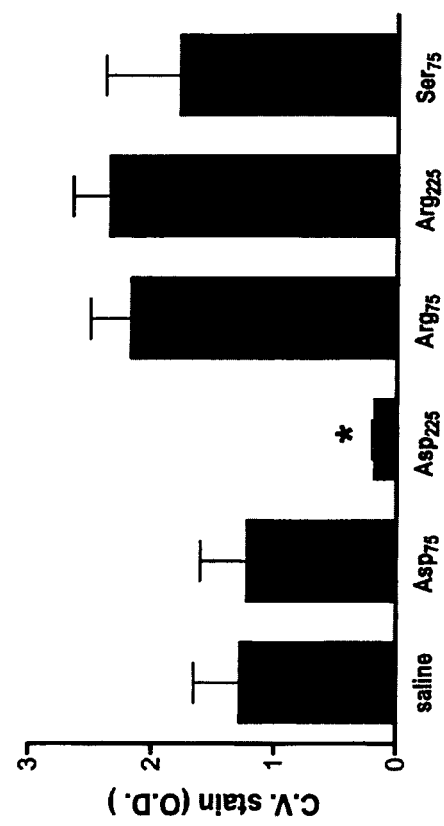

FIG. 11. Dispersion of early *Burkholderia* biofilms by anionic polyamino acids of different lengths.

Figure 12:
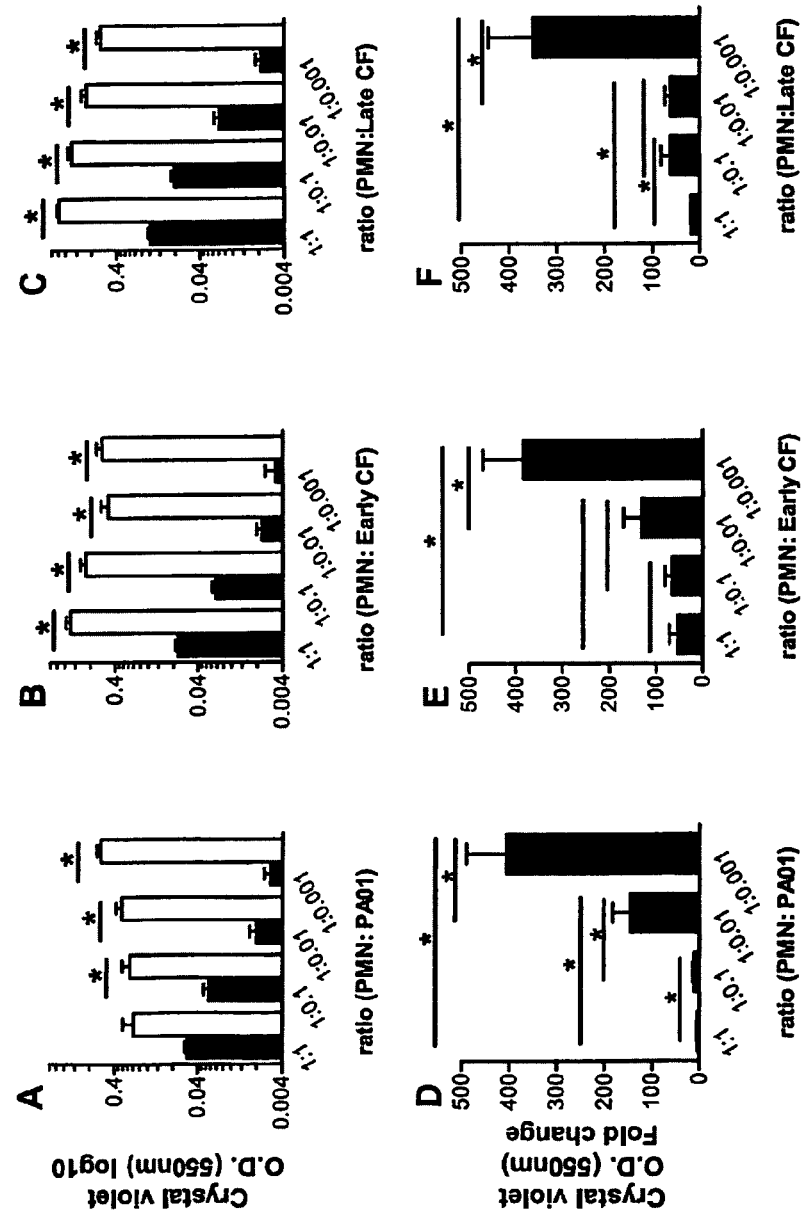

FIG. 12. *P. aeruginosa* biofilm formation is enhanced by human neutrophils. Biofilm density was quantitated by crystal violet (C.V.) staining at 24 hours of bacterial growth in the presence (open bar) or absence (black bar) of neutrophils. At time 0, a fixed innocula of neutrophils ($2.5 \times 10^6$) was combined with *P. aeruginosa* at a 1:1 ratio, and decreasing 10-fold concentrations of bacteria to 1:0.001. Strains examined were the lab standard PAO1 (Panel A), a clinical strain isolated early after initial infection (Panel B) and an isogenic mucoid strain isolated from the same patient four years later (Panel C). Biofilm formation was quantified by C.V. staining with correlated optical density presented on a log 10 scale. Significance of the addition of neutrophils (*) was calculated by students t-test at $p<0.05$, with comparisons as noted. Neutrophil-induced fold changes in biofilm density for each strain was calculated for each concentration ratio (Panels D-F). Background values were subtracted and $P.$ $aeruginosa$+neutrophils average readings were divided by $P.$ $aeruginosa$ average readings. (Panel D) is the fold change of PAO1 (depicted in 1A), (Panel E) is the fold change of Early strain (depicted in 1B), and (Panel F) is the fold change of Late strain (depicted in 1C). Significance (*) was determined with the comparison as noted by one way ANOVA followed by Tukey's post test at $p<0.001$.

Figure 13:
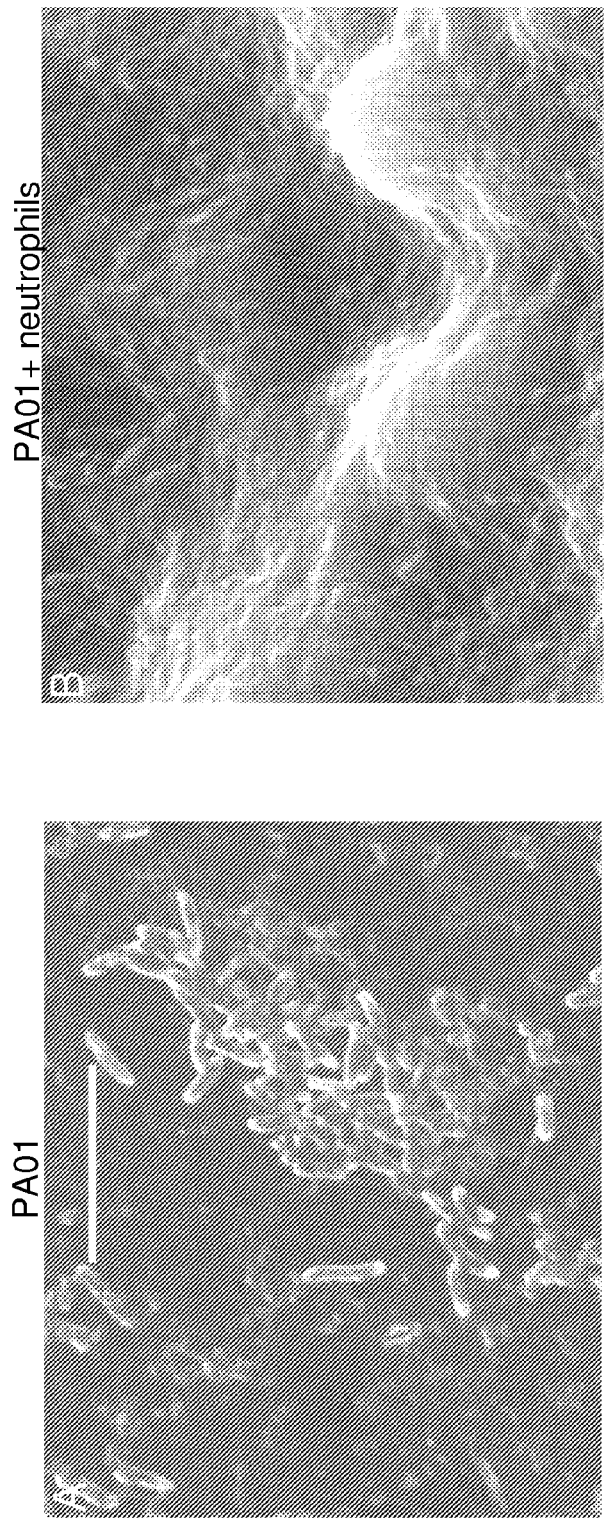

FIG. 13. Scanning electron microscopy (SEM) of neutrophil-induced enhancement of biofilm density and architecture. Biofilms of strain PAO1 were grown for 48 hours in the presence or absence of human neutrophils. Examination by SEM at high magnification demonstrated biofilms grown without human neutrophils were scattered sparsely on the reactor pegs (Panel A), while biofilms grown with neutrophils (Panel B) were much thicker and nearly confluent. Biofilms grown in the presence of human neutrophils have a more established architecture compared to biofilms grown in the absence of neutrophils. Scale bar is 200 µm.

Figure 14:
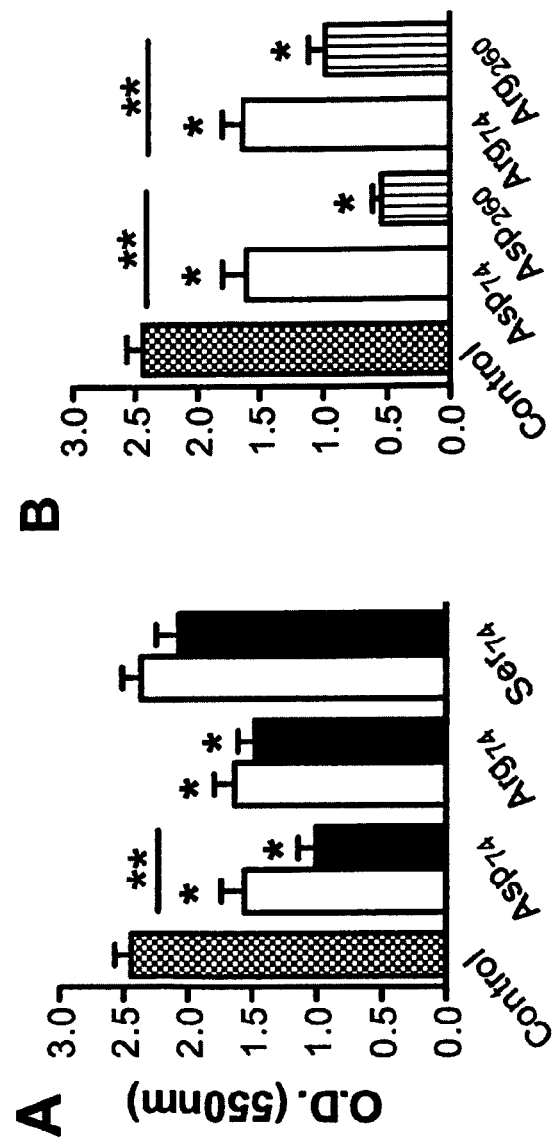

FIG. 14. $P.$ $aeruginosa$ biofilms induced by neutrophils are disrupted by electrostatically charged amino acid chains. Panel A: $P.$ $aeruginosa$ (strain PA01) biofilms formed for 24 hours in the presence of neutrophils were washed in saline and combined with poly(amino acids) of differing length and charge for 3 hours at 37° C. $(Asp)_{74}$ at 5 µM (open bars) exhibited disruption of the biofilm, and this effect was significantly greater at 10 µM (black bars). Addition of $(Arg)_{74}$ at 5 µM (open bars) also induced disruption of the biofilm, although this effect was not significantly greater with 10 µM (black bars). The uncharged $(Ser)_{74}$ had no effect. Panel B: Using poly(amino acids) all at a concentration of 5 ⎕M, the longer $(Asp)_{260}$ was more effective than the shorter $(Asp)_{74}$, and $(Arg)_{260}$ was more effective then $(Arg)_{74}$. All assays are as measured by optical density from C.V. staining. Significance (*) was calculated by one way ANOVA followed by Dunnetts' post test at $p<0.05$ and (**) two-tailed t-test $p<0.05$.

Figure 15:
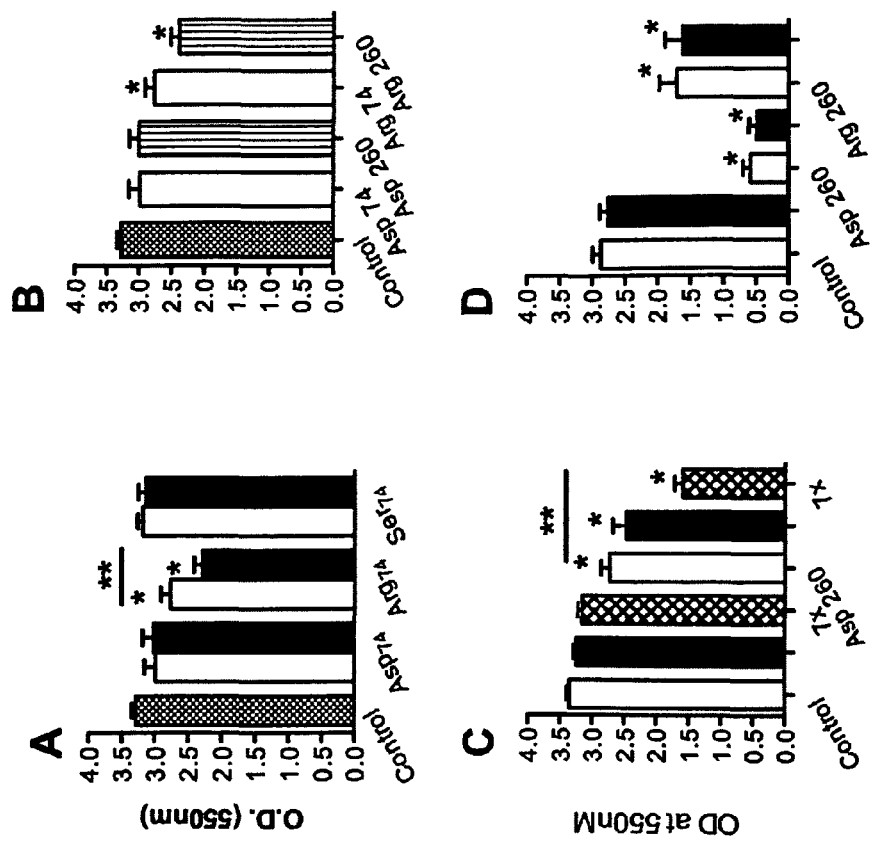

FIG. 15. Proteolytic degradation reduces the capacity of charged poly(amino acids) to disrupt neutrophil-induced $P.$ $aeruginosa$ biofilms. Panel A: When poly(amino acids) of differing concentration were combined with a neutrophil-induced 24 hour $P.$ $aeruginosa$ biofilm in the presence of overnight culture material (OCM), only $(Arg)_{74}$ had a small but significant capacity to disrupt the biofilm at 5 µM (open bars) or 10 µm (black bars). Panel B: Under identical conditions, when the capacity of $(Asp)_{74}$, $(Asp)_{260}$, $(Arg)_{74}$, and $(Arg)_{260}$ to disrupt biofilms was tested, only $(Arg)_{74}$, and $(Arg)_{260}$ had a significant effect in the presence of OCM. Panel C: When $(Asp)_{260}$ (open bars) was combined with a PI cocktail (black bars) in the presence of the OCM, a significant disruption of the biofilm was achieved, that was further increased when the PI concentration was increased to 7-fold (crosshatched bars). Panel D: When the biofilms were removed from the OCM and washed once in saline, both $(Asp)_{260}$ and $(Arg)_{260}$ exhibited a significant disruptive effect (open bars). No enhancement was achieved by the addition of a PI cocktail (black bars) following removal of the neutrophil cellular milieu. All assays are as measured by optical density from C.V. staining. Significance (*) was calculated by one way ANOVA followed by Dunnetts' post test at $p<0.05$ and (**) two-tailed t-test $p<0.05$.

Figure 16:
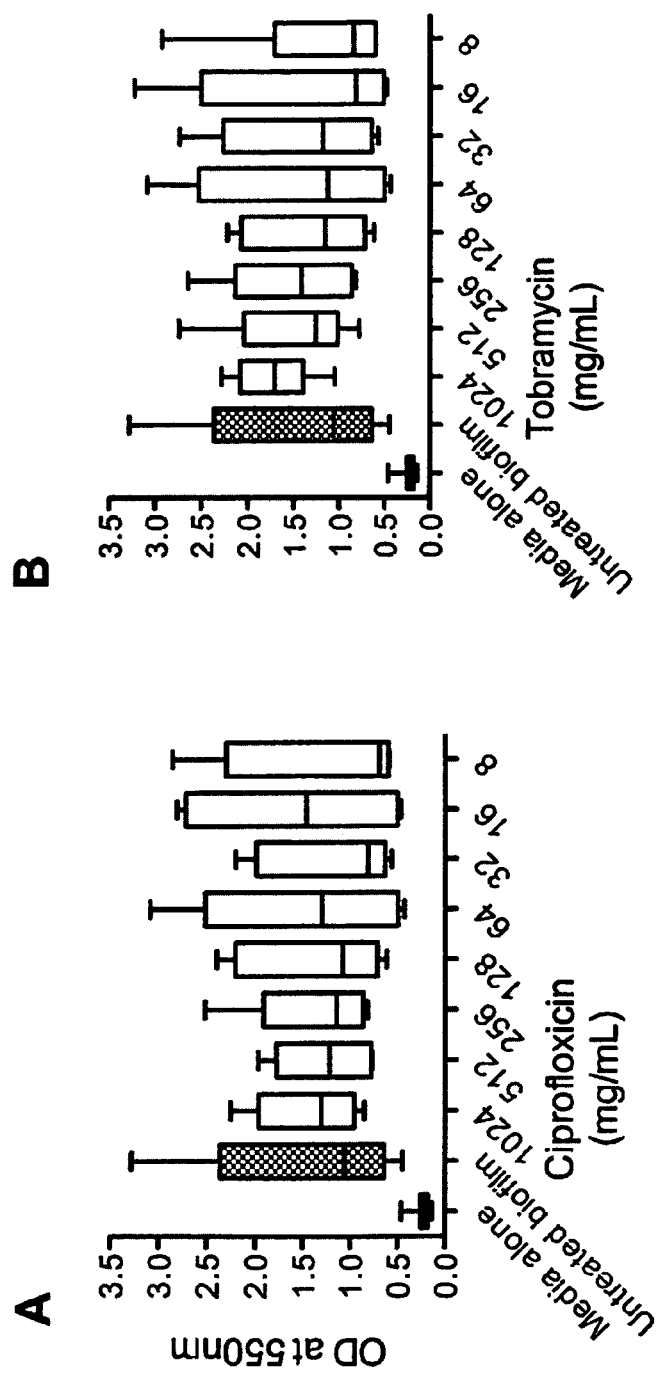

FIG. 16. Neutrophil-induced $P.$ $aeruginosa$ biofilms are not disrupted by antiPseudomonal antibiotics. Neutrophil-induced PAO1 biofilms formed at a 1:0.001 ratio of bacteria to neutrophils were exposed to the antibiotics Ciprofloxicin (Panel A) or Tobramycin (Panel B) for 3 hours at 37° C. at concentrations ranging from 8 µg/mL to 1024 µg/mL. The biofilms density was then quantified by C.V. staining. No disruption of the biofilm was observed in response to either antibiotic over the range of dilutions tested. An untreated biofilm, as well as a media only control, was included to serve as a reference of biofilm formation and background staining. Both assays are as measured by optical density from C.V. staining. Significance (*) was calculated by the Kruskal-Wallis test followed by Dunn's multiple comparison test to the untreated biofilm at $p<0.05$.

Figure 17:
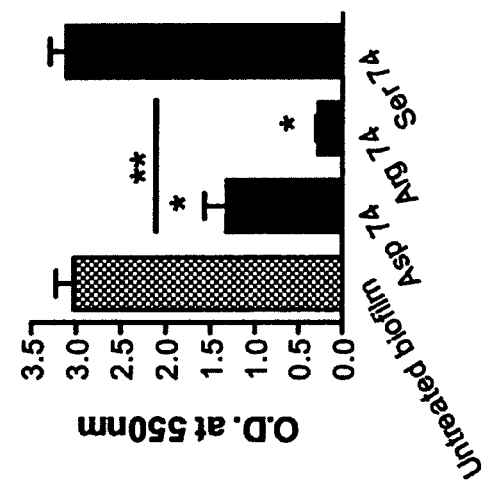

FIG. 17. Charged amino acid chains have the capacity to prevent neutrophil-induced enhancement of $P.$ $aeruginosa$ biofilm formation. Short chain $(Asp)_{74}$, $(Arg)_{74}$ and $(Ser)_{74}$ at 10 µM were added at time=0 to $P.$ $aeruginosa$ PAO1 ($2.5 \times 10^3$ CFU) combined with neutrophils ($2.5 \times 10^6$ CFU). Following 24 hours incubation at 37° C. both $(Asp)_{74}$ and $(Arg)_{74}$ prevented biofilm formation, with poly(Arg) significantly better then poly(Asp). Neutral $(Ser)_{74}$ displayed no effect. Assays are as measured by optical density from C.V. staining. Significance (*) was calculated by one way ANOVA followed by Dunnetts' post test at $p<0.05$ and (**) two-tailed t-test $p<0.05$.

Figure 18:
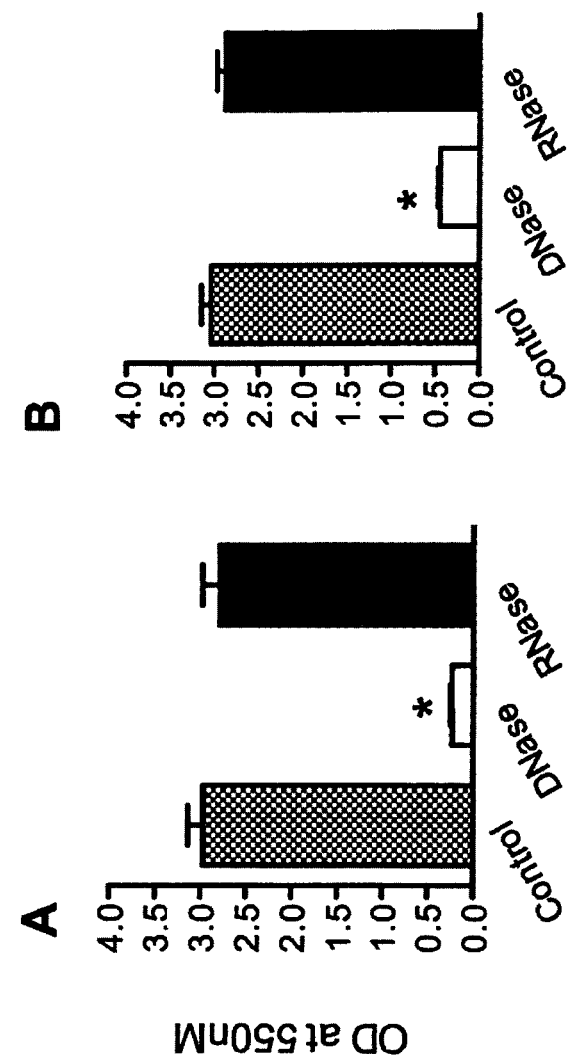

FIG. 18. Neutrophil-induced $P.$ $aeruginosa$ biofilms are both disrupted and prevented by DNase. Panel A: $P.$ $aeruginosa$ strain PAO1 biofilms ($2.5 \times 10^3$ CFU) were grown for 24 hours in the presence of neutrophils ($2.5 \times 10^6$ CFU/mL). The biofilms were then exposed to either DNase (open bars) or RNase (black bars) for 3 hours. The neutrophil-induced biofilm was significantly disrupted by DNase, but not RNase. Panel B: DNase (or RNase) were combined with $P.$ $aeruginosa$ strain PAO1 ($2.5 \times 10^3$ CFU) and neutrophils ($2.5 \times 10^6$ CFU/mL), and a biofilm was allowed to form for 24 hours. The presence of DNase prevented the formation of the biofilm, while RNase had no effect. Assays are as measured by optical density from C.V. staining. Significance (*) was calculated by one way ANOVA followed by Dunnetts' post test at $p<0.05$.

Figure 19:
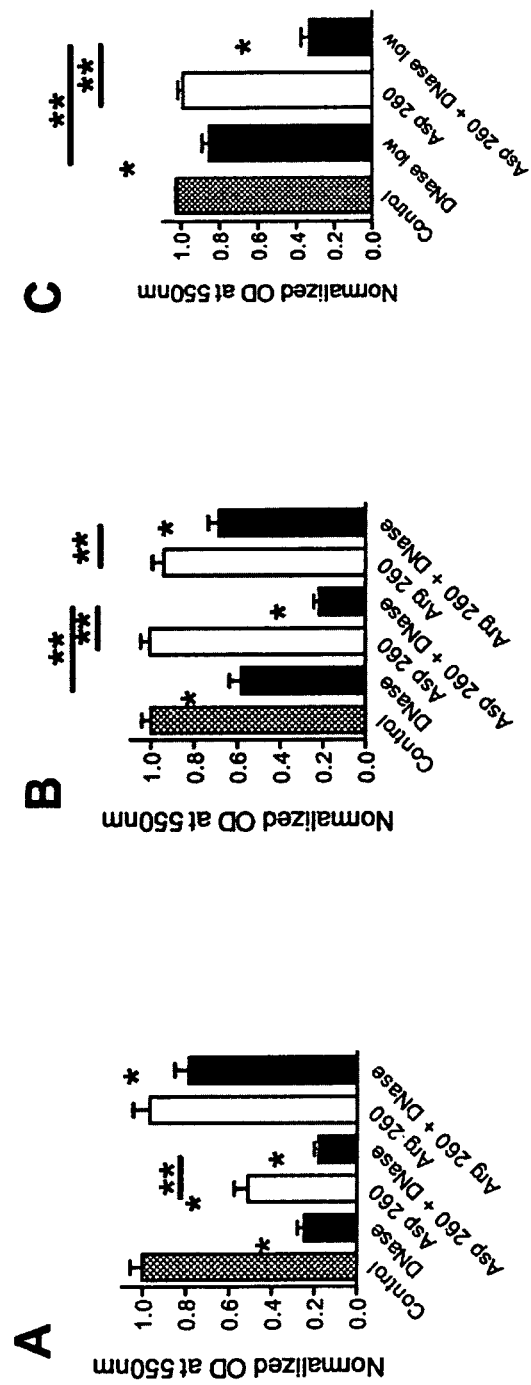

FIG. 19. Poly(aspartic acid) works in a cooperation with DNase to disrupt neutrophil-induced $P.$ $aeruginosa$ biofilms. PA01 biofilms were allowed to form for 24 or 48 hours in the presence of neutrophils at a 1:0.01 ratio of bacteria to neutrophils. The biofilms were then washed in saline and exposed to either a poly(amino acid) alone (open bars) or combined with DNase (black bars). In all experiments, exposure to DNase and/or poly(amino acids) were for 10 minutes at 37° C. in saline. Panel A: As single agents, $(ASP)_{260}$ (5 µM) and DNase (33 µg/mL), but not $(Arg)_{260}$ (5 µM), effectively disrupted 24 hour old biofilms. Panel B: Using a 48 hour biofilm, DNase (33 µg/mL), but not $(ASP)_{260}$ (5 µM) nor $(Arg)_{260}$ (5 µM) was effective as a single agent. However, a significant increase in biofilm disruption was achieved when $(Asp)_{260}$ was combined with DNase. Panel C: Using a 48 hour biofilm and a lower concentration of DNase (8.25 µg/mL), a synergistic effect of $(ASP)_{260}$ (5 µM) and DNase was achieved. Assay is as measured by optical density from C.V. staining. Significance (*) was calculated by one way ANOVA followed by Dunnetts' post test at $p<0.05$ and (**) two-tailed t-test $p<0.05$.

Figure 20:
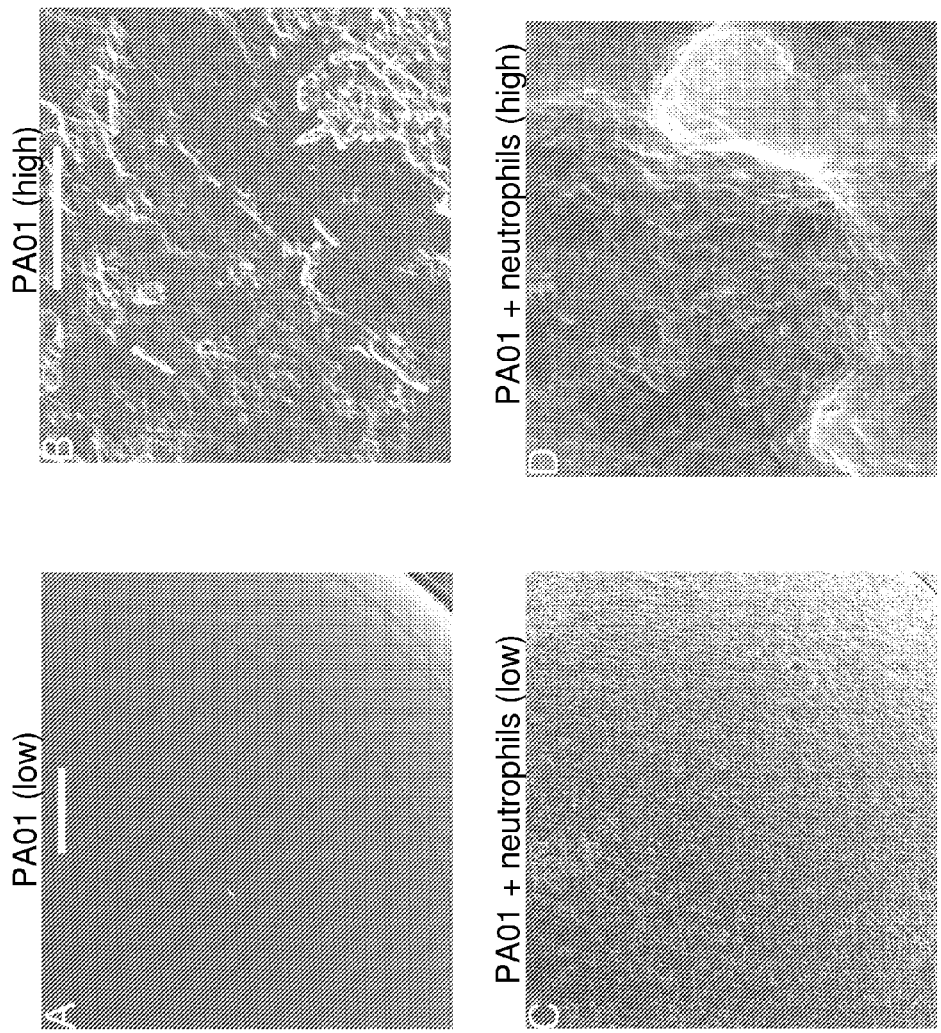

FIG. 20. Scanning electron microscopy (SEM) of neutrophil-induced enhancement of biofilm density and architecture. Biofilms of strain PAO1 were grown for 48 hours in the presence or absence of human neutrophils. Examination by SEM at low magnification demonstrated biofilms grown without human neutrophils were scattered sparsely on the reactor pegs (Panel A), while biofilms grown with neutrophils (Panel C) were much thicker and nearly confluent. Examination at high magnification shows that biofilms grown with human neutrophils (Panel D) have a more established architecture compared to biofilms grown in the absence of neutrophils (Panel B). Scale bar for A and C is 200 µm, for B and D is 5 µm.

Figure 21:
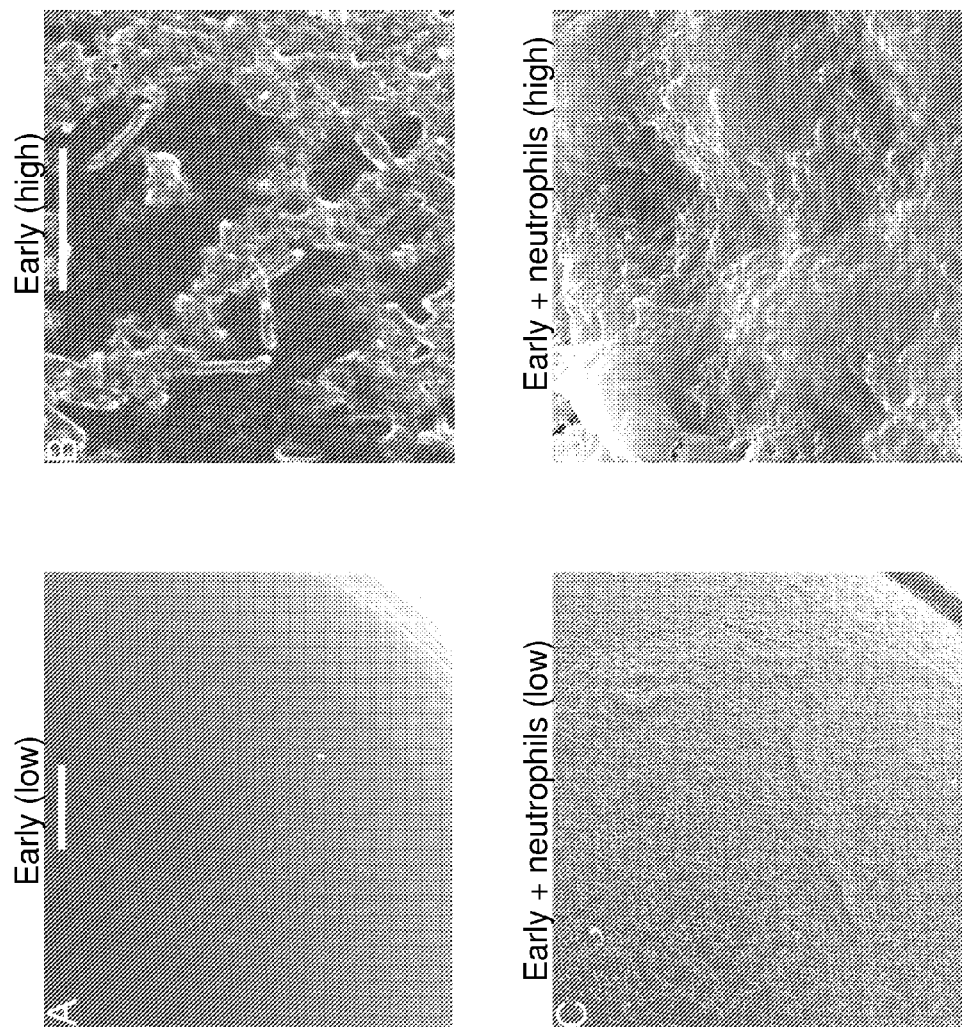

FIG. 21. Scanning electron microscopy (SEM) of neutrophil-induced enhancement of biofilm density and architecture. Biofilms of an Early CF strain were grown for 48 hours in the presence or absence of human neutrophils. Experimental design is identical to Supplemental FIG. 2 (above). Scale bar for A and C is 200 µm, for B and D is 5 µm.

Figure 22:
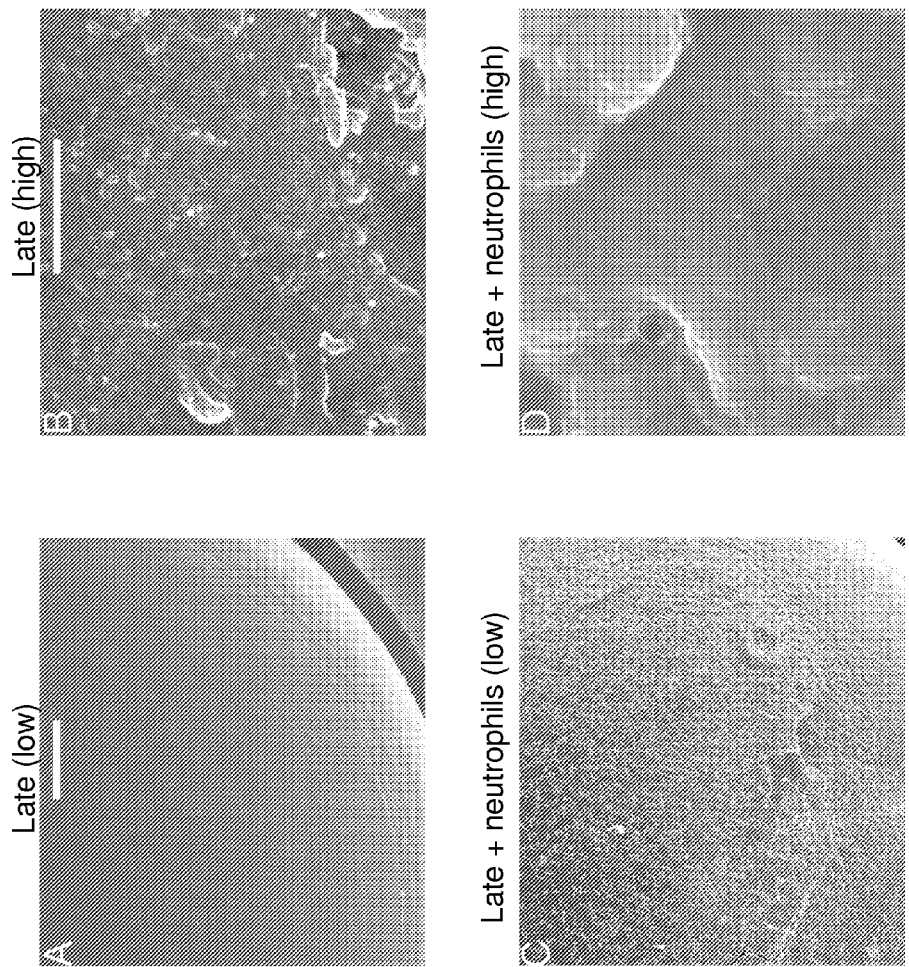

FIG. 22. Scanning electron microscopy (SEM) of neutrophil-induced enhancement of biofilm density and architecture. Biofilms of a Late CF strain were grown for 48 hours in the presence or absence of human neutrophils. Experimental design is identical to Supplemental FIG. 2 (above). Scale bar for A and C is 200 µm, for B and D is 5 µm.

Figure 23:
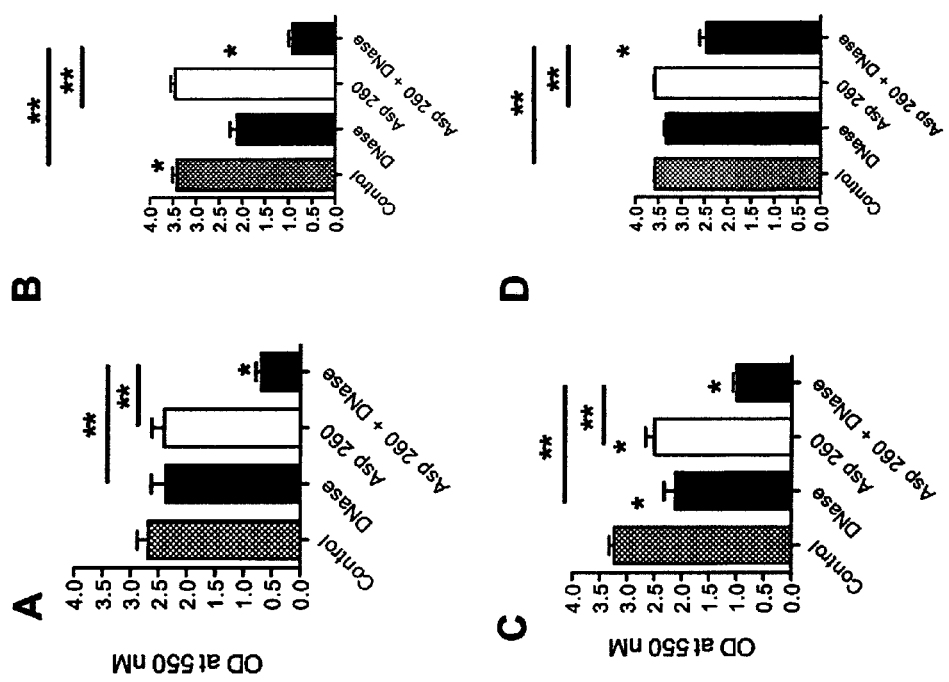

FIG. 23. Poly(aspartic acid) works in a cooperation with DNase to disrupt neutrophil-induced *P. aeruginosa* biofilms from clinical strains. *P. aeruginosa* biofilms from an isogenic Early and Late CF strain were allowed to form for 24 or 48 hours in the presence of neutrophils at a 1:0.01 ratio of bacteria to neutrophils. The biofilms were then washed in saline and exposed to either a poly(amino acid) (5 µM) alone (open bars) or combined with DNase (33 µg/mL) (black bars) for 10 minutes at 37° C. in saline. Panel A: Singly, neither $(Asp)_{260}$ nor DNase, effectively disrupted 24 hour old biofilm of the Early strain. Significant increases in biofilm disruption were achieved when $(Asp)_{260}$ was combined with DNase. Panel B: Using a 48 hour biofilm of the Early strain, DNase, but not $(Asp)_{260}$ was effective as a single agent. Significant increases in biofilm disruption were achieved when $(Asp)_{260}$ was combined with DNase. Panel C: As single agents, both $(Asp)_{260}$ and DNase, effectively disrupted a 24 hour old biofilm of the Late strain. A significantly greater increase in biofilm disruption was achieved when $(Asp)_{260}$ was combined with DNase. Panel D: Using a 48 hour biofilm of the Late strain, neither DNase, nor $(Asp)_{260}$ was effective as a single agent. Significant increases in biofilm disruption were achieved when $(Asp)_{260}$ was combined with DNase. Assay is as measured by optical density from C.V. staining. Significance (*) was calculated by one way ANOVA followed by Dunnetts' post test at $p<0.05$ and (**) two-tailed t-test $p<0.05$.

DESCRIPTION OF THE INVENTION

The present invention generally relates to a composition and method for the inhibition of biofilm formation or reduction of existing or developing biofilms in a subject. In one embodiment, the method comprises administering to a patient that has or is at risk of developing biofilms a compound that associates with a structure of an early biofilm. These aspects of the invention are based on the inventors' discovery that compounds such as polyamino acids can disrupt biofilms and, in particular, neutrophil-enhanced biofilms, by associating with structures within early biofilms. Therefore, interference with the structural components of an early biofilm at the site of infection will inhibit the formation and establishment of biofilms, providing a significant benefit to a patient. In addition, this discovery can be extended to other diseases and conditions associated with biofilm formation, and particularly where neutrophils are involved in an inflammatory response to the disease or condition, and more particularly, when neutrophil association with an inflammatory process is chronic or prolonged.

One of the predominant features of the CF airway is the chronic high-level influx of immune cells. Persistent neutrophil accumulation and necrosis in the CF airways results in sputum highly enriched with DNA, actin, and granule proteins, which are all implicated in the pathogenesis of CF lung disease (1, 16-20). Based on the concept that early CF lung disease features low numbers of planktonic, environmental strains of *P. aeruginosa* entering a neutrophil-rich airway (4), the present inventors tested the effect of neutrophils on the earliest stages of *P. aeruginosa* biofilm formation using a concentration of neutrophils compatible with the quantity of cells present in the airways of CF children prior to persistent *P. aeruginosa* infection, and concentrations of *P. aeruginosa* consistent with early infection (2, 21).

*Pseudomonas* infections of the cystic fibrosis airway persist due to the formation of biofilms. As the formation of biofilms is facilitated by the presence of neutrophils (specifically neutrophil-derived DNA and F-actin) (22), the present inventors also examined the possibility of disrupting the framework of the resulting biofilm. Charged cationic molecules, such eosinophil granule proteins have potent antimicrobial properties in some settings (23, 24). However, strongly cationic compounds have the capacity to be injurious to both the infection as well as the host. Recently, it has been shown that polyanionic peptides have the capacity to disrupt DNA/histone, as well as F-actin/histone complexes (25). If the framework of the induced biofilm is a result of the DNA with associated histones, which then serve as a linker to the F-actin filaments, the addition of polyanionic or polycationic compounds may serve as a mechanism to disrupt a biofilm based on electrostatic competition.

The present inventors have also found a novel method for quantifying the effect of neutrophils on the early stages of *P. aeruginosa* biofilm development with a relatively high-throughput assay. Using this method, the present inventors examined the effect of neutrophils on *P. aeruginosa* biofilm development over a wide range of bacterial concentrations, with both the laboratory strain PA01 and a well-characterized isogenic early (non-mucoid) and late (mucoid) strain of *P. aeruginosa* recovered from the airway of a patient with CF. In this context, the present inventors have found that compounds such as, for example, polyamino acids can disrupt neutrophil-enhanced biofilms.

These finding demonstrate the capacity of human neutrophils to enhance the early formation of biofilms formed by *Pseudomonas aeruginosa*. This enhancement is a concentration dependent phenomenon, where the lowest MOI (1:1000) of *P. aeruginosa* to neutrophils results in the largest level of enhancement. These findings may relate to the scenario where low inoculums of environmental *P. aeruginosa* are introduced into a neutrophil-rich environment, such as the CF-airway. The concentration of neutrophils ($1.6 \times 10^7$ per mL) used in this analysis was based on previous BAL sampling of the airways of infants with CF prior to persistent *P. aeruginosa* infection where neutrophil recovery ranged from ($10^4$ to $10^6$ per mL) with an estimated recovery rate of 1-2% (1-3, 30).

The mechanism of this enhancement is centered primarily on the products released from the dying neutrophil. In settings of exuberant inflammation, the neutrophil has a lifespan of only a few hours and the clearance of dying cells is generally impaired. This inflammatory milieu contains both neutrophil-originated chromosomal DNA as well as F-actin, both of which are highly concentrated in the sputum of patients with cystic fibrosis. These polymers, though both negatively charged, rapidly become linked via positively charged histones (and other proteins) and cations. The resulting structure provides a matrix that can be utilized by *P. aeruginosa* for enhanced progression though the early stages of biofilm growth.

As the enhancement of biofilm formation can be related to a charged based effect, the disruption of biofilms may also be based on electrostatic effects. To test this, the present inventors utilized both long (~260 mer) and short (~75 mer) amino acid chains of varying charge. Without being bound to one theory, it is believed that the concentrated, and relatively sterically small, negative charge of polyamino acids such as polyaspartic acid (poly(D)) sequester the histone from the DNA and F-actin. This then causes the biofilm to disassociate even at very low concentrations of poly(D). Extending the charge hypothesis, positively charged polyamino acids such as polyarginine (poly(R)) complex with negatively charged materials, such as the DNA and F-actin portions of the biofilm. An added benefit of the poly(D) is the lack of reported toxicity. The present inventors have demonstrated the disruption of a biofilm with polyamino acids and also that the presence of protease inhibitors can augment this disruption.

Preventing biofilm formation with amino acids can be particularly effective when the polyamino acids are charged. The present inventors have shown that both anionic and cationic polyamino acids are effective at reducing the formation of biofilms, and are even more effective in the presence of protease inhibitors. Cationic polyamino acids such as poly(R) may have the added effect of killing bacteria within the biofilm, thus increasing its ability to prevent biofilm formation.

*P. aeruginosa* biofilm formation in the CF airways appears to occur in the context of stagnant mucous plugs, which are lodged in the airway lumen, and are largely composed of dead and dying neutrophils (31, 32). The model of biofilm development described herein recreates static biofilm growth and also has the advantage of being relatively fast and high throughput in comparison to other systems of biofilm study.

A biofilm is generally defined herein as a community of microorganisms attached to a solid surface. A biofilm community can include bacteria, fungi, yeasts, protozoa, and other microorganisms. More specifically, a biofilm is a surface-attached community of microbial cells encased within a self-produced extracellular polysaccharide matrix that exhibits properties different from the planktonic microbial counterparts. Biofilms that are commonly found associated with human tissue and organ surfaces are frequently bacterial biofilms. In cystic fibrosis, by way of example, both *Pseudomonas aeruginosa* and *Burkholderia cepacia* infect and form biofilms in the lungs of patients having the disease. Other examples of microorganisms that form biofilms in tissues or on medical devices or dressings include, but are not limited to: *Streptococcus sanguis*, *E. coli*, and *Streptococcus viridans*.

While many biofilms are associated with diseases in humans and other animals the present invention is applicable to all manner of biofilms. Biofilms may also occur outside of the body, such as in industrial, commercial or wastewater treatment settings. For instance, biofilms foul cooling towers, contaminate papermaking machinery, corrode drinking water mains, contaminate equipment used in the food and beverage industry and sour oil fields with acid by-products. The compounds of the present invention may be used to prevent or disrupt these biofilms.

Examples of bacteria that may be found associated with biofilms include gram-negative bacteria such as, but not limited to: *Escherichia coli, Proteus mirabilis, Klebsiella pneumoniae, Pseudomonas aeruginosa, Burkholderia cepacia, Klebsiella oxytoca, Providentia stuartii*, or *Serratia marcescens* and gram-positive bacteria such as, but not limited to: *Enterococcus faecalis*, Vancomycin Resistant Enterococci (VRE), *Streptococcus viridans, Staphylococcus epidermidis*, and *Staphylococcus aureus* or *Staphylococcus saprophyticus*. These bacteria are commonly found associated with medical devices including catheters. Examples of fungi that may be found associated with biofilms include *Candida albicans, Candida parapsilosis*, and *Candida utilis*. Compounds and compositions according to the invention can be used to prevent or inhibit the growth and proliferation of biofilms associated with these microorganisms.

Biofilms are often associated with DNA and other cellular components (such as F-actin) that are released from dying cells. Certain biofilms, such as those associated with *Pseudomonas aeruginosa* infections, are facilitated by the release of these cellular components from dying neutrophils and lead to serious and often life-threatening conditions. In addition to cystic fibrosis, *P. aeruginosa* biofilms develop in other clinical settings, such as eye infections in contact lens wearers or severe wounds and burns.

For example, *P. aeruginosa* infections can lead to bacterial keratitis, a biofilm infection that develops on the eyes of contact lens wearers, wherein both the contact lens and the eye of the subject are infected by *P. aeruginosa*. The presence of neutrophils can cause a large increase in the infection of the lens. Compounds and compositions of the present invention may thus be used to treat or prevent *P. aeruginosa* infections of the eyes and on contact lenses. For example, compounds of the present invention may be added to commercial contact lens solutions to prevent biofilm formation. Any type of contact lens may be treated with the compounds and compositions of the present invention, including disposable, daily wear or extended wear contact lenses.

*P. aeruginosa* infections, and resulting biofilms, also frequently develop in patients with severe burns and wounds. Compounds and compositions of the present invention may thus be used to treat or prevent *P. aeruginosa* biofilms associated with severe burns and wounds.

The method of the present invention can be used to treat any patient (subject, individual, animal) that has, is developing (biofilm formation is clinically evident or detectable to the skilled artisan, but has not yet fully formed), or is at risk of developing (no biofilm formation is yet detectable to the clinician or skilled artisan, but the subject is known to be at risk of developing a biofilm due to disease or the pending performance of a treatment, such as a graft implantation) a biofilm. The term "patient" typically refers to a subject that is to be treated or is being treated by a clinician (doctor, nurse, or other medical practitioner) for a disease, condition, procedure, or routine examination (i.e., the patient need not be ill or otherwise suffering from any disease or condition to be treated). However, as used herein, the terms "patient", "subject", "individual" and "animal" can be generally be used interchangeably with reference to the subject to which a compound of the invention is to be administered.

Microbial biofilms can form in and on a variety of tissues as well as on or in a variety of devices and materials that may be used during the treatment of a subject for a particular disease or condition. For example, the method of the present invention can be used to prevent or reduce biofilm formation, or to reduce existing or developing biofilms that may form in connection with a disease or condition in an organ, tissue or body system including, but not limited to, lung, urinary tract, head and neck, vascular system, bone, skin, abdomen. Biofilms may also form on the surface of a tissue, organ or bodily part including, but not limited to, lung, medium airways, ureter, urethra, bladder, prostate, mouth, ear, heart valve, vein, joint, bone, skin, and bile duct. Biofilms may form in connection with a disease or condition including, but not limited to: infectious kidney stones, cystitis, catheter-related infection (kidney, vascular, peritoneal), medical device-related infections, prostatitis, dental caries, chronic otitis media, cystic fibrosis, bronchiectasis, bacterial endocarditis, Legionnaire's disease, orthopedic implant infection, osteomyelitis, wounds, acne, and biliary stents. All of these scenarios are encompassed by the present invention.

Preferably, the compound is administered to a subject (patient, individual, animal) prior to the development of a biofilm, or at the earliest time that biofilm development is suspected or detected. Without being bound by theory, the present inventors believe that the method of the present invention will be particularly effective when used as a preventative or early stage inhibition of biofilm formation. For example, the method of the invention can be used when a patient is suspected to have or be developing a disease or condition associated with the formation of biofilms, where the method is used when the diagnosis is made or early treatment is performed (e.g., prior to the establishment of biofilms in the patient, although there may be detectable evidence of biofilm formation). A young patient diagnosed with cystic fibrosis, for example, may develop biofilms after several years of the disease, but during the earlier diagnosis and treatment stages, the method of the invention may prevent or reduce the formation of the biofilms as the disease advances in the patient. As another example, the method of the present invention may be applied to a prosthetic graft or used in a patient receiving the graft prior to or during the implantation or utilization of the graft. Similarly, the method of the present invention can be used prior to or during use of a catheter by a patient, by applying the compound to the catheter and/or on the tissue contacting or near the catheter. The compound could also be applied to the site of a wound or to the wound dressing when the wound is initially and subsequently treated, or the compound can be applied to a medical device that contacts a patient tissue surface prior to or during use of the medical device by a patient.

Examples of devices that can be treated using the compounds and compositions of the invention include medical devices such as tubing, catheters, pacemakers, prosthetic heart valves, prosthetic joints, voice prostheses, contact lenses, and intrauterine devices. Devices such as pipes, manufacturing machinery, food and beverage equipment, and other devices or surfaces contaminated with or susceptible to contamination with biofilms may be treated using the compounds and compositions of the invention.

Medical devices include disposable or permanent or indwelling catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts, heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field.

Medical devices also include any device which may be inserted or implanted into a human being or other animal, or placed at the insertion or implantation site such as the skin near the insertion or implantation site, and which include at least one surface which is susceptible to colonization by biofilm embedded microorganisms.

Medical devices for the present invention include surfaces of equipment in operating rooms, emergency rooms, hospital rooms, clinics, and bathrooms. Implantable medical devices include orthopedic implants, which may be inspected for contamination or infection by biofilm embedded microorganisms using endoscopy. Insertable medical devices include catheters and shunts, which can be inspected without invasive techniques such as endoscopy.

The present inventors have discovered that certain compounds associate with structures of early biofilms and thereby disrupt existing biofilms or the initial formation of biofilms. Without being bound to one theory, it is believed that electrostatic interactions are involved in the framework structure of a biofilm. For example, negatively charged DNA and F-actin polymers interact with positively charged histones within a biofilm to provide a framework for the biofilm. Therefore, compounds capable of electrostatic competition with the charged components of the biofilm framework may be used to disrupt a biofilm. Charged compounds that associate with structures of early biofilms can include natural or synthetic charged molecules, including natural or synthetic charged polymers. For example, charged natural polymers such as polyamino acids or polynucleotides as well as charged synthetic polymers such as peptide nucleic acids may be used in the present invention. Combinations of natural and synthetic charged molecules are also suitable for the present invention. The compounds may also be modified in ways that alter the charge or stability of the compound. For example, the compound may be phosphorylated to increase the net negative charge of the compound. As another example, the compound may be PEGylated to increase solubility or reduce degradation when administered to a subject. Examples of techniques useful for the synthesis of polymers can be found in Gibney et al., Synthesis of novel proteins, 1997, *Current Opinion in Chemical Biology* 1:537-42, the contents of which are incorporated by reference in their entirety.

In certain embodiments, the charged compounds that associate with structures of early biofilms can be polyamino acids. Polyamino acids suitable for use in the present invention can be composed of synthetic or naturally occurring amino acids, both of which are well known in the art. A polyamino acid can be generally defined as a polymer of the same amino acids or is composed of a series of peptide repeating units, which is intended to mean that an amino acid sequence of two or more amino acid residues is sequentially repeated two or more times in the peptide or protein in uninterrupted succession. Polyamino acids include derivatized polyamino acids. Polyamino acids useful in the present invention can include polyamino acids that are fused to, conjugated to, or otherwise linked to other agents.

Polyamino acids that are particularly effective at disrupting biofilms include, but are not limited to, polyamino acids composed of cationic and anionic amino acids. Examples of anionic polyamino acids include polyaspartic acid (poly(D)) and polyglutamic acid (poly(E)), while examples of cationic polyamino acids include polyarginine (poly(R)), polylysine (poly(K)) and polyhistidine (poly(H)).

In some embodiments, the polyamino acids of the present invention may comprise a combination of charged (i.e., anionic or cationic) and uncharged (i.e., neutral, such as serine) amino acids. The charged and uncharged amino acids may be present in any combination provided the overall polymer has a net negative or positive charge. For example, an aspartic acid residue may be alternated with a serine residue to provide a polyamino acid with an overall negative charge. In alternate embodiments, the polyamino acids may contain from about 25% to about 100% charged amino acids, from about 25% to about 50% charged amino acids, from about 50% to about 75% charged amino acids, from about 75% to about 100% charged amino acids, or from about 85% to about 95% charged amino acids.

The present invention encompasses polyamino acids of any length suitable for administration to a subject. For example, polyamino acids may comprise from about 5 to about 500 amino acids, from about 10 to about 400 amino acids, from about 25 to about 300 amino acids, from about 50 to about 250 amino acids, or from about 75 to about 150 amino acids. In some embodiments, the polyamino acids may comprise about 10, 25, 50, 75, 100, 125, 150, 175, 200, 225, 260, 300, 350, 400, or 500 amino acids. In still other embodiments, the polyamino acids may comprise less than 10 amino acids or more than 500 amino acids.

In certain embodiments of the present invention, the charged compounds that associate with structures of early biofilms can also be administered with one or more protease inhibitors. Protease inhibitors are well known in the art and any protease inhibitor suitable for administration to a subject may be used with the present invention. Examples of protease inhibitors include, but are not limited to, leupeptin, aprotinin, pepstatin A, or combinations thereof. In other embodiments, the charged compounds that associate with structures of early biofilms may be designed to be resistant to the effect of proteases. For example, the compounds may be synthetic polymers that are not susceptible to protease activity. Alternatively, protease-sensitive polymers may be modified by techniques known in the art to render the polymers more resistant to protease activity. Examples of these art-recognized techniques can be found in Twaites et al., Synthetic polymers as drugs and therapeutics, 2005, *Journal of Materials Chemistry* 15:441-455, the contents of which are incorporated by reference in their entirety.

Additional embodiments of the present invention further comprise administering to the patient, either directly or by application to a carrier, implant, catheter, medical device, or tissue or wound dressing, a compound that inhibits the formation or polymerization of actin microfilaments or depolymerizes actin microfilaments, at or proximal to the site of biofilm formation. The method can further comprise, or alternatively include, a compound that inhibits the accumulation of, necrosis of, and/or release of cellular content of cells that undergo necrosis, at or proximal to the site of bacterial infection and/or biofilm formation. The method can further comprise, in combination with one or more of the compounds above, the administration of an anti-DNA compound and/or an anti-mucin compound and/or another compound that is useful for the prevention and/or treatment of a disease or condition in the patient, or that is useful in connection with a procedure being performed on the patient. A detailed description of the additional components described above can be found in U.S. Patent Publication No. 2006/0030359, which is incorporated herein by reference in its entirety.

Preferably, the cells that undergo necrosis and are targeted by the method of the invention are neutrophils, although other types of cells that can undergo necrosis at a site of microbial infection are also included in the invention. For example, such other cells include, but are not limited to, airway epithelial cells or other epithelial cells, macrophages, monocytes, lymphocytes, eosinophils, and the infectious microbe itself (e.g., *P. aeruginosa*).

Without being bound by theory, since virtually every eukaryotic cell contains significant quantities of actin, it is possible that other necrotic cells, in addition to neutrophils, could enhance *P. aeruginosa* biofilm development. Therefore, the present invention is not limited to the inhibition of the accumulation of, necrosis of, or release of the cellular contents of, neutrophils, but rather is extended to other necrotic cells that are present at a site of a microbial infection. For example, in a severe skin burn *P. aeruginosa* could conceivably utilize actin and DNA from necrotic epithelial cells. Similarly, the present invention is not limited to the inhibition of biofilms associated with bacterial infection, as other microbes can also form biofilms.

For the inhibition of the formation or polymerization of actin microfilaments (or depolymerization of the actin microfilaments), compounds preferably inhibit F-actin, which is the microfilament form of actin, and can also be referred to herein as "anti-actin" compounds. A variety of compounds that affect the polymerization and depolymerization of actin filaments are well known in the art. A detailed description of various classes of such compounds, as well as specific compounds and their known actions on actin is provided in Meijer et al., 2003, *Progress in Cell Cycle Research* 5:511-525, which is incorporated herein by reference in its entirety. Classes of compounds that can be used in the present invention include, but are not limited to, cytochalasins, latrunculins, misakinolides, swinholides, myacolides, spinxolides, and scytophycins. Specific compounds which are useful in a product/composition/formulation of the present invention include, but are not limited to, cytochalasin B, cytochalasin D, latrunculin A, misakinolide A, swinholide A, myacolide B, spinxolide, scytophycin, domain 1 of gelsolin, destrin or profilin. Other suitable anti-actin compounds will be known to those of skill in the art or can be identified using standard actin polymerization assays (e.g., see Meijer et al., supra) and such compounds are encompassed for use in the present invention.

For the inhibition of neutrophil accumulation, necrosis and/or release of cellular content, or for the inhibition of many other necrotic cell types targeted by the invention (cells that can undergo necrosis at the site of a microbial infection), any anti-inflammatory compound or any compound that interferes with a neutrophil's (by way of example) ability to adhere to or near a site of infection by biofilm-associated microbe, to migrate to such site, or to sense or respond to chemoattractants at or near such site (or that would result in migration of the neutrophil to such site), is encompassed by the present invention. For example, such compounds can inhibit or reduce the release or biological activity of chemoattractants, cytokines, or chemokines at or near (proximal to) the site of infection that would otherwise attract a neutrophil, cause it to migrate to the site of infection, or allow or enhance neutrophil adherence at or near the site of infection. Administration of such anti-inflammatory/anti-neutrophil compounds early in the disease process that is associated with biofilm formation is believed to be an important aspect of the invention. Therefore, anti-inflammatories/anti-neutrophil compounds would be administered upon the initial diagnosis of the disease or condition that is associated with biofilm formation, and preferably prior to a significant formation of biofilms in the patient.

Such compounds are well known in the art and include, but are not limited to, cytokine inhibitors, chemokine inhibitors, chemoattractant inhibitors, fluoroquinolones, Cox inhibitors, leukotiene receptor antagonists, leukotriene synthesis inhibitors, inhibitors of the p38 MAP kinase pathway, and glucocorticoids. More specifically, compounds that are useful in this embodiment of the invention include, but are not limited to: any inhibitor of eicosanoid synthesis and release, including any Cox-2 inhibitor; Cox-1 inhibitors; inhibitors of some certain prostaglandins (prostaglandin E(2); PGD(2)), inhibitors of certain leukotrienes ($LTB_4$); classes of antibiotics with known direct or indirect anti-inflammatory effects, including macrolides (e.g. azithromycin) and fluoroquinolones (e.g., levofloxacin; moxifloxacin; gatifloxacin); inhibitors of p38 MAP kinase; antagonists of growth factors which regulate neutrophil release, including granulocyte colony-stimulating factor (G-CSF) (e.g., antibodies or antigen binding fragments thereof, G-CSF antagonist variants or mimetics, drugs that antagonize the function of G-CSF); antagonists of granulocyte-macrophage colony-stimulating factor (GM-CSF); inhibitors of the function of cytokines and chemokines, including antagonists of tumor necrosis factor (TNF), antagonists of interleukin-8 (IL-8); transforming growth factor beta (TGF-beta); antibodies that block sites of neutrophil adhesion and thereby limit neutrophil accumulation to sites of inflammation, including anti-beta2 integrins (e.g., anti-CD11/CD18) and anti-ICAM-1; and neutrophil inhibitory material from other organisms, (e.g., excretory-secretory (ES) material from the parasitic nematode *Nippostrongylus brasiliensis*).

In one embodiment, a product, composition or formulation of the present invention also includes an anti-DNA compound. According to the present invention, an anti-DNA compound is any compound that causes the destabilization or degradation of DNA. Such compounds are known in the art and include, but are not limited to, nucleases, hydroxyl radical generating compounds, and the like. For example, DNase I or rhDNase (Pulmozyme; Genentech, USA) is a well-known anti-DNA compound that is useful in the present invention. Compounds suitable for the degradation of DNA will be known to those of skill in the art and all are encompassed by the present invention.

In another embodiment, a product, composition or formulation of the present invention also includes an anti-mucin compound. Mucins are a family of large, heavily glycosylated proteins. Some mucins are membrane bound due to the presence of a hydrophobic membrane-spanning domain that favors retention in the plasma membrane, but many mucins are secreted on mucosal surfaces and in saliva. Anti-mucin compounds include any compound that causes the destabilization or degradation of mucin, or inhibits the interaction of mucin with other compounds or molecules. Such compounds include, but are not limited to, antibodies and antigen binding fragments thereof that bind to mucin, sulphatases, glycosidases, and proteases.

In another embodiment, a product, composition or formulation of the present invention also includes one or more compounds that are useful for treating a particular disease or condition that is associated with biofilm formation. For example, when the patient has or is suspected of having cystic fibrosis, the polyamino acid compound can also be used in conjunction with other drugs or therapeutic compounds that are conventionally used to treat cystic fibrosis. As another example, when the patient has a wound, the polyamino acid compound can be applied to the wound dressing, along with other compounds, such as anti-microbial compounds, or administered concurrently with such compounds by a different route. As yet another example, patients receiving a prosthetic graft may be receiving anti-rejection drugs, anti-microbials, or growth factors to enhance the establishment of the graft or growth of appropriate tissue at the graft site, and the polyamino acid compound of the invention can be administered in connection with such treatments.

In one embodiment, the compounds and compositions of the present invention may be administered with any known treatment for the disease or condition associated with the targeted biofilm or microorganisms associated with the biofilm. For example, the compounds and compositions of the present invention may be administered with antiPseudomonal compounds such as antibiotics effective for treating *P. aeruginosa* infections.

According to the present invention, the present invention can use any one, two, three, four, or more compounds from any class listed above, including any combination of the compounds. For example, in one embodiment, the method uses a polyamino acid and an anti-actin microfilament compound and/or an anti-DNA compound and/or an anti-mucin compound. Alternatively, the method uses both a polyamino acid compound and an anti-neutrophil (or other necrotic cell) compound. In further embodiments, additional compounds that are useful for the treatment of a particular condition or disease in the patient to be treated can be included.

According to the present invention, an "antagonist" or an "anti"-compound or agent (e.g., a polyamino acid, an anti-actin microfilament compound, an-anti-neutrophil compound, an anti-DNA compound or an anti-mucin compound) refers to any compound which inhibits (e.g., antagonizes, reduces, decreases, blocks, reverses, or alters) the effect of a given protein or compound. More particularly, an antagonist is capable of acting in a manner relative to the given protein's or compound's activity, such that the biological activity of the given protein or compound, is decreased or blocked in a manner that is antagonistic (e.g., against, a reversal of, contrary to) to the natural action of the given protein or compound. Antagonists can include, but are not limited to, an antibody or antigen binding fragment thereof, a protein, peptide, nucleic acid (including ribozymes and antisense), or a product of drug/compound/peptide design or selection that provides the antagonistic effect.

Compounds useful in the present invention also include compounds that are products of rational drug design, natural products, and compounds having partially defined regulatory properties. A regulatory agent, including an antagonist of a given protein, can be a protein-based compound, a carbohydrate-based compound, a lipid-based compound, a nucleic acid-based compound, a natural organic compound, a synthetically derived organic compound, or an antibody, or fragments thereof. In one embodiment, such regulatory agents of the present invention include drugs, including peptides, oligonucleotides, carbohydrates and/or synthetic organic molecules which regulate the production and/or function of one or more proteins in the alternative complement pathway. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies*, Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

An antibody or antigen-binding fragment thereof useful in the present invention selectively binds to a protein and thereby blocks or inhibits the activity of the protein. According to the present invention, the phrase "selectively binds to" refers to the ability of an antibody, antigen-binding fragment or binding partner to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention. A bi-specific (or multi-specific) antibody is capable of binding two (or more) antigens, as with a divalent (or multivalent) antibody, but in this case, the antigens are different antigens (i.e., the antibody exhibits dual or greater specificity). A bi-specific antibody suitable for use in the present method includes an antibody having: (a) a first portion (e.g., a first antigen binding portion) which binds to a given protein; and (b) a second portion which binds to a second protein.

The invention also extends to non-antibody polypeptides, sometimes referred to as antigen binding partners or antigen binding polypeptides, that have been designed to bind selectively to and cause the neutralization or inhibition of a protein according to the present invention. Examples of the design of such polypeptides, which possess a prescribed ligand specificity are given in Beste et al. (*Proc. Natl. Acad. Sci.* 96:1898-1903, 1999), incorporated herein by reference in its entirety.

An isolated nucleic acid molecule that is useful as an antagonist includes, but is not limited to, an anti-sense nucleic acid molecule, a ribozyme or siRNA. As used herein, an anti-sense nucleic acid molecule is defined as an isolated nucleic acid molecule that reduces expression of a protein by hybridizing under high stringency conditions to a gene encoding the protein. Such a nucleic acid molecule is sufficiently similar to the gene encoding the protein that the molecule is capable of hybridizing under high stringency conditions to the coding or complementary strand of the gene or RNA encoding the natural protein. RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. A ribozyme is an RNA segment that functions by binding to the target RNA moiety and inactivate it by cleaving the phosphodiester backbone at a specific cutting site.

An isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated nucleic acid molecule can be isolated from its natural source or produced using recombinant DNA technology (e.g., polymerase chain reaction (PCR) amplification, cloning) or chemical synthesis.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

In one embodiment of the invention, a method is provided to identify compounds that are useful in the method of inhibiting the formation of biofilms, particularly those that are enhanced by necrotic cells such as neutrophils, or reducing existing or developing such biofilms. This method includes the steps of: (a) contacting a putative inhibitory compound with a microbial culture in the presence and absence of a population of cells or a lysate thereof; and (b) measuring biofilm formation after contact with the putative regulatory compound as compared to in the absence of the compound and as compared to in the presence and absence of the population of cells or lysate thereof. A decrease in biofilm formation in the presence of the putative regulatory compound and the presence of the population of cells or lysate thereof, as compared to in the absence of the population of cells or lysate thereof and as compared to in the absence of the putative regulatory compound, indicates that the putative regulatory compound inhibits necrotic cell-enhanced biofilm formation or reduces necrotic cell-enhanced biofilms. In this embodiment of the invention, the microbial culture must be a microbial culture that can form biofilms, but the culture is provided in a planktonic state prior to contact with the putative inhibitory compound. In addition, the population of cells used in this assay are selected because they can undergo necrosis in the presence of the microbial cells. For example, as shown in the examples, neutrophils will undergo necrosis in the presence of a culture of *P. aeruginosa*. These are only exemplary microbe and cell combinations that can be used. Other combinations will be apparent to those of skill in the art. The assay of the invention is designed to identify compounds that inhibit biofilm formation that is associated with or enhanced by the necrosis of cells at the site of infection or biofilm formation. In one embodiment, the assay is designed to identify additional polyamino acids that are effective in other methods of the invention.

Microbial cells for use in this invention are any microbial cells that are capable of forming biofilms under some conditions, and particularly, including in the presence of necrotic cells or the components thereof (e.g., actin microfilaments or DNA) as described herein. Preferably, formation of biofilms and aggregation of the microbial cells is enhanced by the necrotic cells or components thereof. The microbial cells are not required to be of the same strain, species, genus, or even microbe, although this is preferred. Microbial cells that form biofilms can include, but are not limited to, bacteria, fungi, yeasts, and protozoa, with bacteria being particularly preferred. Bacteria that are particularly useful in this method of the invention include, but are not limited to, any of the previously described biofilm forming bacteria, such as *P. aeruginosa, Burkholderia cepacia, Streptococcus sanguis, E. coli,* and *Streptococcus viridans*. In one embodiment, particular strains or mutants of a microbial cell can be used in the assay to identify compounds that impact necrotic cell-enhanced biofilm formation that may be relevant to a particular strain of microbial cell carried by a specific patient or subset of patients, or to focus the identification of the inhibitor on a particular characteristic or expression of a particular gene or protein in the microbial cell that affects necrotic cell-enhanced biofilm formation. In one embodiment, the cells can be labeled with a detectable label (e.g., green fluorescent protein).

Populations of cells (or the lysates thereof) to be used in the present invention include any cells that can undergo necrosis in the presence of a microbial cell as described above. For example, such cells include, but are not limited to, neutrophils, airway epithelial cells or other epithelial cells, macrophages, monocytes, lymphocytes, eosinophils, and the infectious microbe itself (e.g., *P. aeruginosa*). Cell lysates can be produced using any methods known to those of skill in the art, including any means of disrupting, permeabilizing or otherwise lysing of cell membranes to release the intracellular contents. In one embodiment, the cells can be labeled with a detectable label.

As used herein, the term "test compound", "putative inhibitory compound" or "putative regulatory compound" refers to compounds having an unknown or previously unappreciated regulatory activity in a particular process. As such, the term "identify" with regard to methods to identify compounds is intended to include all compounds, the usefulness of which as a regulatory compound for the purposes of regulating biofilm formation is determined by a method of the present invention.

The conditions under which a microbial cell are contacted with a putative regulatory compound according to the present invention, such as by mixing, plating, etc., are conditions in which the microbial cell is not forming a biofilm (i.e., the microbial culture is in a planktonic state) if essentially no regulatory compound is present. The conditions under which the population of cells that can undergo necrosis are contacted with a putative regulatory compound are conditions under which the majority of cells in the population of cells are viable and not undergoing necrosis.

The present methods involve contacting cells and/or lysates with the compound being tested for a sufficient time to allow for interaction of the compound with the microbial cells and/or the population of cells or components in the lysate thereof. The period of contact with the compound being tested can be varied depending on the result being measured, and can be determined by one of skill in the art. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring.

The final step in the method is to measure biofilm formation or a parameter associated with biofilm formation in the presence and absence of the putative regulatory compound and in the presence and absence of the population of cells. Since the present method is designed to identify compounds that impact necrotic cell-enhanced biofilm formation (although the compound may also affect biofilm formation in the absence of necrotic cells), a candidate compound is identified as useful if it inhibits biofilm formation to a greater degree (detectable, and preferably, statistically significantly greater) in the presence of the necrotic cells as compared to in the absence of the necrotic cells. Statistical analysis to determine differences between controls and test cultures can be performed using any methods known in the art, including, but not limited to, Student's t test or analysis of variance for continuous variables. Statistical significance is typically defined as $p<0.05$.

In another, or additional embodiment, one can detect the effect of the putative regulatory compound on the binding of the microbial cells to actin and/or DNA from the population of necrotic cells, or on the aggregation of microbial cells in the presence of the population of necrotic cells.

Methods of evaluating biofilm formation are well known in the art and are described in the Examples. For example, confocal microscopy, microscopy, and static biofilm assays. Methods of measuring actin and DNA binding are also well known in the art and are described in the Examples.

Agonists and antagonists identified by the above methods or any other suitable method are useful in the therapeutic or biofilm-inhibition methods as described herein.

Compounds useful in the present invention are typically provided in the form of a composition (formulation). In one embodiment of the invention, a pharmaceutical composition or formulation is prepared from an effective amount of a compound of the invention and a pharmaceutically acceptable carrier. Pharmaceutically acceptable carriers are well known to those with skill in the art. According to the present invention, a "pharmaceutically acceptable carrier" includes pharmaceutically acceptable excipients and/or pharmaceutically acceptable delivery vehicles, which are suitable for use in the administration of a formulation or composition to a suitable in vivo site. A suitable in vivo site includes any site wherein biofilms have formed, are forming, or may form. Pharmaceutically acceptable carriers may be capable of maintaining a compound used in a formulation of the invention in a form that, upon arrival of the compound at the target site in a patient, the compound is capable of acting, preferably resulting in a therapeutic benefit to the patient.

One type of pharmaceutically acceptable carrier includes a controlled release formulation that is capable of slowly releasing a composition of the present invention into a patient. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other suitable carriers include any carrier that can be bound to or incorporated with the compound that extends half-life of the compound to be delivered. A carrier can be modified to target to a particular site in a patient, thereby targeting and making use of a compound at that site.

In one embodiment, a compound useful in the present method is administered in a formulation suitable for aerosol delivery. Carriers that are particularly useful for aerosol delivery according to the present invention include, but are not limited to: dry, dispersible powders; small capsules (e.g., microcapsules or microparticles); liposomes; and nebulized sprays. Dry, dispersible powders suitable for aerosolized delivery of compounds are described in detail in U.S. Pat. No. 6,165,463, incorporated herein by reference in its entirety (See also products from Inhale Therapeutic Systems, Inc. and Quadrant Technology). Suitable liposomes for use in aerosols include any liposome, and particularly, any liposome that is sufficiently small to be delivered by aerosol in the method of the invention. Microcapsules and microparticles are known in the art. For example, Alliance Pharmaceutical Corporation has a particle engineering technology, called PulmoSphere, prepared by a proprietary spray-drying process and are designed to be both hollow and porous. A product by Ventolin consists of micronized albuterol (free base) particles suspended in a mixture of CFC-based propellants. Proventil HFA contains micronized albuterol sulfate and a small percentage of an ethanol co-solvent to solubilize the stabilizing oleic acid surfactant. Devices for delivery of aerosolized formulations include, but are not limited to, pressurized metered dose inhalers (MDI), dry powder inhalers (DPI), and metered solution devices (MSI), and include devices that are nebulizers and inhalers.

In another embodiment, a compound useful in the present method is administered in a formulation suitable for topical delivery. Such formulations include any lotion, excipient, cream, gel, or other topical carrier suitable for topical administration.

For injection, the compounds of the invention can be formulated in appropriate aqueous solutions, such as physiologically compatible buffers such as Hanks's solution, Ringer's solution, or physiological saline buffer.

For transmucosal and transcutaneous administration, penetrants appropriate to the barrier to be permeated can be used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

The compounds can be formulated for parenteral administration by injection, e.g., by bolus injection or continuous infusion. Formulations for injection can be presented in unit dosage form, e.g., in ampoules or in multi-dose containers, with an added preservative.

The compounds can also be formulated in rectal compositions such as suppositories or retention enemas, e.g., containing conventional suppository bases such as cocoa butter or other glycerides.

In accordance with the present invention, determination of acceptable protocols to administer a compound (product, agent, composition, formulation), including the route of administration and the effective amount of a compound to be administered to a patient, can be accomplished by those skilled in the art. A compound of the present invention can be administered in vivo or ex vivo. Suitable in vivo routes of administration can include, but are not limited to, oral, nasal, inhaled, topical, intratracheal, transdermal, rectal, and parenteral routes. Parenteral routes can include, but are not limited to, subcutaneous, intradermal, intravenous, intramuscular, and intraperitoneal routes. Topical routes include inhalation by aerosol (i.e., spraying) or topical surface administration to the skin of a patient, or to a dressing, device, catheter, prosthetic graft or other product to be placed into contact with a patient tissue surface. The compound may be administered by nasal, inhaled, intratracheal, topical, or systemic routes (e.g., intraperitoneal, intravenous). Ex vivo refers to performing part of the administration step outside of the patient.

The compound can be administered directly to or proximal to the site of biofilm formation or potential therefore. For example, the biofilm can be administered by surgical or clinical procedure directly to the tissue, organ, bodily part, or to a material or device that is to be (or anticipated to be) at or proximal to a site in the patient where a biofilm may form, is likely to form, or will form. By way of example, in one aspect, the compound is administered to the lung or airways of the patient. In another aspect, the compound is applied to a prosthetic graft or administered to the patient receiving the graft prior to or during the implantation or utilization of the graft. In another aspect, the compound is applied to a catheter prior to or during use of the catheter by a patient. In yet another aspect, the compound is applied to the site of a wound or to the wound dressing when the wound is treated. A compound may also be applied to a medical device that contacts a patient tissue surface prior to or during use of the medical device by a patient. Other types of administration or application of the compound and method of the invention will be apparent to those of skill in the art given this discussion.

An effective amount is any amount of the compound that causes a detectable reduction in biofilm formation as compared to in the absence of the compound, or reduces existing biofilms or developing biofilms as compared to in the absence of the compound. A single dose of an agent, including proteins, small molecules and antibodies, for use in a method described herein, may comprise between about 0.01 microgram×kilogram$^{-1}$ and about 10 milligram×kilogram$^{-1}$ body weight of an animal. A single dose of an agent may also comprise between about 1 microgram×kilogram$^{-1}$ and about 10 milligram×kilogram$^{-1}$ body weight of an animal, between about 5 microgram×kilogram$^{-1}$ and about 7 milligram×kilogram$^{-1}$ body weight of an animal, between about 10 microgram×kilogram$^{-1}$ and about 5 milligram×kilogram$^{-1}$ body weight of an animal, or between about 0.1 milligram×kilogram$^{-1}$ and about 5 milligram×kilogram$^{-1}$ body weight of an animal, if the an agent is delivered by aerosol. A single dose of an agent may comprise between about 0.1 microgram× kilogram$^{-1}$ and about 10 microgram×kilogram$^{-1}$ body weight of an animal, if the agent is delivered parenterally. In some embodiments, the compounds are administered at concentrations of from about 0.5 to about 50 µM, such as, for example 1 µM, 5 µM, 10 µM, 20 µM or 40 µM.

In one embodiment, an appropriate single dose of a nucleic acid, when delivered with a liposome carrier, can be from about 0.1 µg to about 100 µg per kg body weight of the patient to which the complex is being administered. In another embodiment, an appropriate single dose can be from about 1 µg to about 10 µg per kg body weight. In alternate embodiments, an appropriate single dose of nucleic acid:lipid complex can be at least about 0.1 µg of nucleic acid, at least about 1 µg of nucleic acid, at least about 10 µg of nucleic acid, at least about 50 µg of nucleic acid, or at least about 100 µg of nucleic acid.

One of skill in the art will be able to determine that the number of doses of a compound to be administered to an animal is dependent upon the extent of the biofilm formation and the underlying condition or disease of which biofilm formation is a symptom or a component, and the response of an individual patient to the treatment. In addition, the clinician will be able to determine the appropriate timing for delivery of the compound in a manner effective to inhibit biofilm formation or reduce biofilms in the patient. The compound may be delivered within between about 1 hour and 48 hours of the diagnosis or confirmation by a clinician of the risk or likelihood of developing biofilms or a condition or disease that is associated with the development of biofilms, or the as soon as an infection has been identified that would be likely to be associated with biofilms, or as soon thereafter as practical in order to inhibit biofilm formation before it develops or before it begins to have a deleterious effect on the patient. When a medical device (graft, catheter, stent, wound dressing, prosthetic) is to be introduced into contact with a patient tissue surface, the compound can be administered prior to, concurrently with, or substantially immediately after the patient is contacted with the device, graft or dressing. In one embodiment, the compound is administered as soon as it is recognized (i.e., immediately or in a few hours or days) by the patient or clinician that the patient may be at risk of or developing biofilms. Such administrations can be given until the patient is no longer at risk of developing biofilms or at least until signs of biofilm inhibition or prevention occur. The compound can be administered within at least 15 minutes, 30 minutes, 45 minutes, 1 hour, 2 hours, 3 hours, or any increment of 0.25 hours from 0.25 hours (15 minutes) to 72 hours prior to or after the diagnosis, procedure or treatment of the patient. The compound can be administered subsequently, routinely, or as needed to prevent, control or reduce biofilm formation or reduce existing or developing biofilms in the patient.

Typically, it is desirable to obtain a therapeutic benefit in a patient. A therapeutic benefit is not necessarily a cure for a particular disease or condition, but rather encompasses a result that can include alleviation of the disease or condition, elimination of the disease or condition, reduction of a symptom associated with the disease or condition (e.g., biofilm formation), prevention or alleviation of a secondary disease or condition resulting from the occurrence of a primary disease or condition, and/or prevention of the disease or condition or reoccurrence of the disease or condition. A beneficial effect can easily be assessed by one of ordinary skill in the art and/or by a trained clinician who is treating the patient. The term, "disease" refers to any deviation from the normal health of the individual and includes a state when disease symptoms are present, as well as conditions in which a deviation (e.g., infection, gene mutation, genetic defect, etc.) has occurred, but symptoms are not yet manifested. As used herein, the phrase "protected from a disease" refers to reducing the symptoms of the disease; reducing the occurrence of the disease, and/or reducing the severity of the disease. Protecting a patient can refer to the ability of a compound or composition of the present invention, when administered to a patient, to prevent a condition from occurring and/or to cure or to alleviate the symptoms of the disease or condition, signs or causes. As such, to protect a patient from a disease includes both preventing disease occurrence (prophylactic treatment) and treating a patient that has a disease (therapeutic treatment) to reduce the symptoms of the disease. More specifically, protecting a patient from biofilm formation can refer to preventing the formation or development of a biofilm and/or to reduce or eliminate existing biofilms in the patient. To treat a patient refers to the act of applying the method of the invention to any suitable patient (subject, individual, animal).

The methods of the present invention can be used in any subject, including a cell, tissue or organism. Suitable subjects may include any animal (patient, subject, individual), and particularly, any animal of the Vertebrate class, Mammalia (i.e., mammals), including, without limitation, primates, rodents, livestock and domestic pets. Preferred mammals to which the present method can be applied include humans.

Various aspects of the present invention are described in the following experiments. These experimental results are for illustrative purposes only and are not intended to limit the scope of the present invention.

EXAMPLES

The following Materials and Methods were used in the examples below.

Bacterial Strains, Media, and Culture Conditions

The bacterial strains and origins used in this study are listed in Table 1. All *P. aeruginosa* strains were obtained from stock plates of Luria Broth agar (LB), grown overnight in Cellgro RPMI 1640 with L-glutamine (Mediatech, Inc, Herndon, Va.) supplemented with 2% Heat Inactivated (Human) Platelet Poor Plasma (HIPPP) at 37° C. with moderate shaking (225 rpm) overnight and frozen down to achieve consistent growth phase. All assays utilized bacteria grown overnight from the frozen stock in RPMI+2% HIPPP at 37° C. as detailed above. Cultures were then equilibrated in a Beckman DU 640 spectrophotometer (Fullerton, Calif.) at 650 nM to an OD of 0.30 ($5 \times 10^8$ CFU/mL). Serial 10 fold dilutions of the cultures took place in RPMI.

TABLE 1

| Parent | Strain | Features | Refrence or Origin |
| --- | --- | --- | --- |
| *P. aeruginosa* | PAO1 | Lab standard | BH Iglewski |
| *P. aeruginosa* | Early | Clinical isolate, days after initial infection | Ogle et al. 1987 |
| *P. aeruginosa* | Late | Clinical isolate, 4 years after initial infection | Ogle et al. 1987 |

Neutrophil Isolation

Neutrophils for all assays were isolated from healthy volunteers by the plasma Percoll method as previously described (26).

Crystal Violet Biofilm Assay

Test strains were grown from frozen stocks and equilibrated and diluted as described above. Donor neutrophils were resuspended at a concentration of $17.24 \times 10^6$/mL in RPMI+2% HIPPP. A volume of 145 µL of this suspension was gently placed in a Nunc round bottom 96 well plate (Rochester, N.Y., cat #163320). The cellular control was a plate identical to the test plate, save for the absence of neutrophils. Dilutions of bacteria at OD 0.3 (1:1 ratio to neutrophils) to a 1:1000 dilution thereof were added to the wells in a volume of 5 µL (for a total well volume of 150 µL). A Nunc TSP lid system (cat #445497) was then placed on the 96 well plate. This assembly was then incubated for 24 hours with rocking (3-4 oscillations/minute) at 37° C. At 24 hours, the peg lids with bacterial biofilms were removed and rinsed for 2 minutes in sterile normal saline to remove non-adherent bacteria and cellular debris. The Nunc TSP system was air dried for 5 minutes, then fixed for 10 minutes in 100% ethanol. The ethanol was evaporated for 5 minutes on bench top, then stained in 1% crystal violet for 15 minutes. Excess crystal violet was removed by 2 rinses in normal saline. Decolorization took place in a Nunc 96 well flat bottom plate 96 (cat #269787) with 200 µL 100% methanol/well for 45 minutes. Readings were taken in a µQuant plate reader using the KCjunior v1.403 software at 550 nM (Bio-tek instruments, inc., Winooski, Vt.). Values within samples were averaged prior to comparison to the control plate.

Quantification of Biofilm Density

To quantify the density of biofilms formed under various conditions biofilms were established on a NUNC Tsp plate lid as detailed above. Pegs were rinsed in saline for 2 minutes, then placed in a 96 well round bottom Nunc plate with 150 µL sterile saline, and sonicated twice for 10 minutes in a Fisher FS 110 sonicator (Pittsburgh, Pa.). Test wells were pooled, and serially diluted 10 fold, and 20 µL was plated in triplicate at the $1 \times 10^{-3}$ to $1 \times 10^{-6}$ dilutions onto LB agar for quantization.

PCR of *P. aeruginosa* Genes to Verify Isogenic Status

Reactions conditions and primers are as described by Onteniente et al. (27). Taq polymerase was Eppendorf mastermix (Hamburg, Germany, cat #0032 900.410-01). Primers were purchased from IDT (Coralville, Iowa).

Amino Acid Treatment Preparation

Pure amino acid chains of multiple lengths were obtained from Sigma and initially diluted in PCR grade $dH_2O$ to 1M, then serially diluted in normal saline. Amino acids used were poly(D) (Sigma, St. Louis, Mo., cat #P5387, P6762), poly(R) (Sigma, cat #P7762, P4663), poly(S) (MP biomedicals, Solon, Ohio, cat #104898). No further purification was preformed. Protease inhibitor cocktail set III (Calbiochem, San Diego, Calif., cat #539134) was used at full strength, Pepstatin A (resuspended concentration of 1 mg/mL) (Sigma, cat #P5318). Pulmozyme (DNase) (Genentech, South San Francisco, Calif., NDC#50242-0100-40) at 1 mg/mL in saline. Leupeptin was made from a stock (Sigma, cat #L8511) and diluted at a final concentration of 5 ug/mL. Aprotinin was made from a stock (Sigma, A4529) and diluted at a final concentration of 5 ug/mL. Treatments or prevention treatments were added per well as follows of DNase (5 µl), Poly (amino) acids (5 µl), Aprotinin (0.38 µL), Leupeptin (0.38 µL), protease inhibitor cocktail (1.5 µL), Pepstatin A (0.15 µL)

Verification of Isogenic Status of Early and Late CF *P. aeruginosa* Isolates

In order to establish lineage of the strains that we utilized in this assay a series of PCR reactions were run that amplify Variable Number Tandem Repeats (VNTR's) (27). Briefly, this method amplifies tandem repeats of nucleotides of defined size that occur in variable number that is related to lineage of the bacteria. Thus, products of similar weights indicate a closer a lineage.

Figure 1:
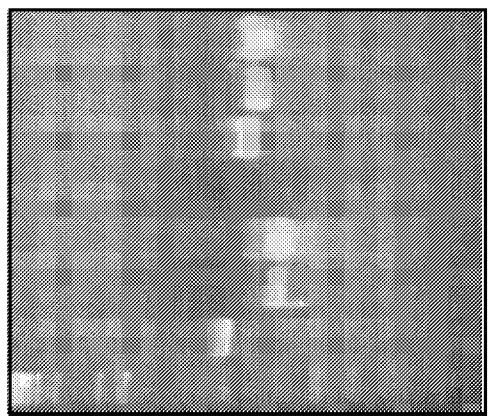
FIG. 1. Multiple variable tandem repeat genotyping shows that the Early and Late *P. aeruginosa* strains are related, where PAO1 is not. Early and Late in 3% agarose gels (A&B), as well as 2% gels (C) show that the two temporally divergent strains are the same bacterium different only in time of isolation. PAO1 in these gels does not produce a similarly weighted product, as it is of a different strain. This is further displayed in (D) where the primers produce a product from PAO1 but neither Early or Late strains do. Ladder is a 1 kb+ladder.
Figure 1:
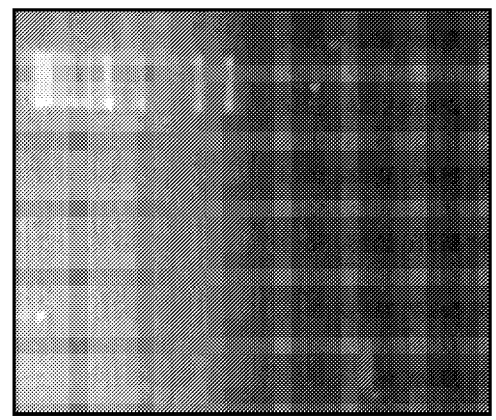
Figure 1:
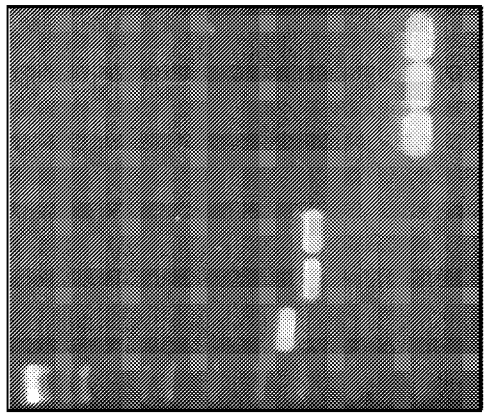
Figure 1:
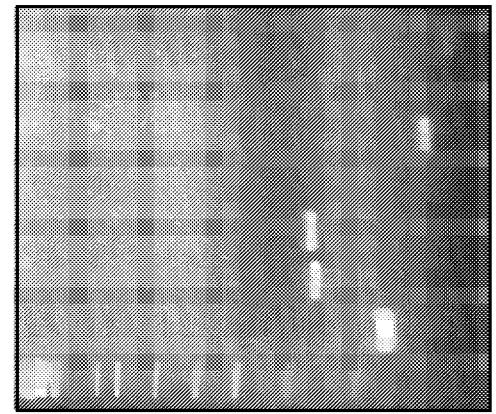

This assay resulted in seven of eight primers providing a product, and all of the reaction products of the Early and Late strains were identical (see FIG. 1). The control, PAO1; a divergent strain, was similar to the two clinical strains in only one product. Coupled with previously published pulse-field data (28), the data indicate that these strains represent isogenic bacteria that have been isolated both at initial colonization, as well as after prolonged infection.

Statistical Analysis

Data was analyzed using the Prism 4 (Graphpad version 4.03, San Diego, Calif.), or Excel (Microsoft Office 2003, Redmond Wash. Student's t-test was used to determine significance of data paired data. One way, repeated measures ANOVA was preformed on data where multiple testing resulted in data sets that required more stringent analysis. Tukey's post test, where all data sets are compared to each other, was used as appropriate as noted, with significance at a value no less than $P<0.05$. Dunnett's post test, where all data sets are compared to the control set was utilized appropriately as noted, with significance at a value no less than $P<0.05$.

Example 1

The following example demonstrates the increase in *Pseudomonas aeruginosa* biofilm density in the presence of human neutrophils.

Human neutrophils isolated from healthy volunteers without further ex vivo stimulation were combined with *P. aeruginosa* strain PA01 (FIG. 2A), Early CF isolate (FIG. 2B), and Late CF isolate (FIG. 2C) over a 4-log ratio of bacteria to neutrophils. All ratios of bacteria with neutrophils tested resulted in a significant ($p<0.05$) enhancement of biofilm density when compared to *P. aeruginosa* of equal concentration grown in the absence of neutrophils, as measured by crystal violet staining.

In the absence of neutrophils, decreasing the amount of bacteria (ranging from $2.5 \times 10^6$ to $2.5 \times 10^4$) resulted in a significant decrease the amount of biofilm present when compared to the higher concentration at each concentration level by one-way ANOVA followed by Tukey's post test. At the 1:100 ($2.5 \times 10^4$ CFU) concentration level, it appears that a basal level of infection is reached due to the very low level innocula and that a decrease to a 1:1000 ($2.5 \times 10^3$ CFU) level does not significantly lower the amount of biofilm formed further in the 24 hour time period (FIGS. 2A-C).

Figure 2A:
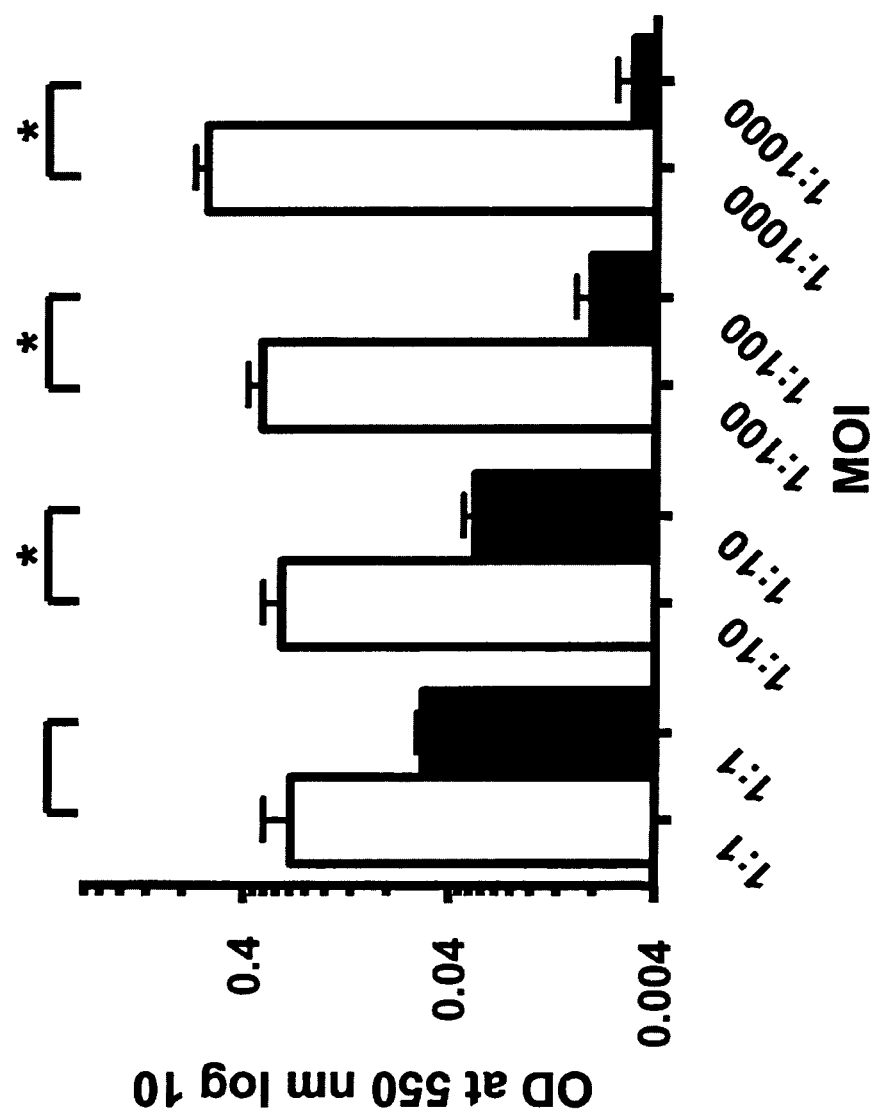
Figure 2B:
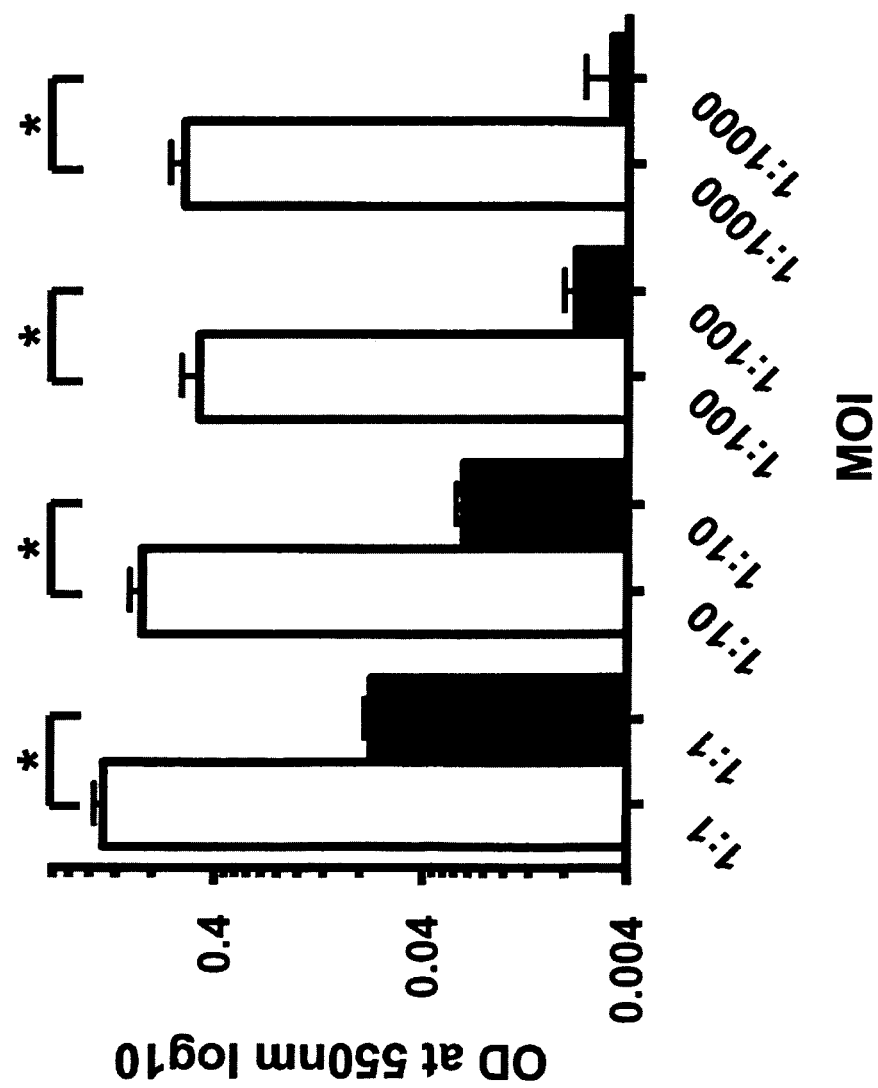
Figure 2C:
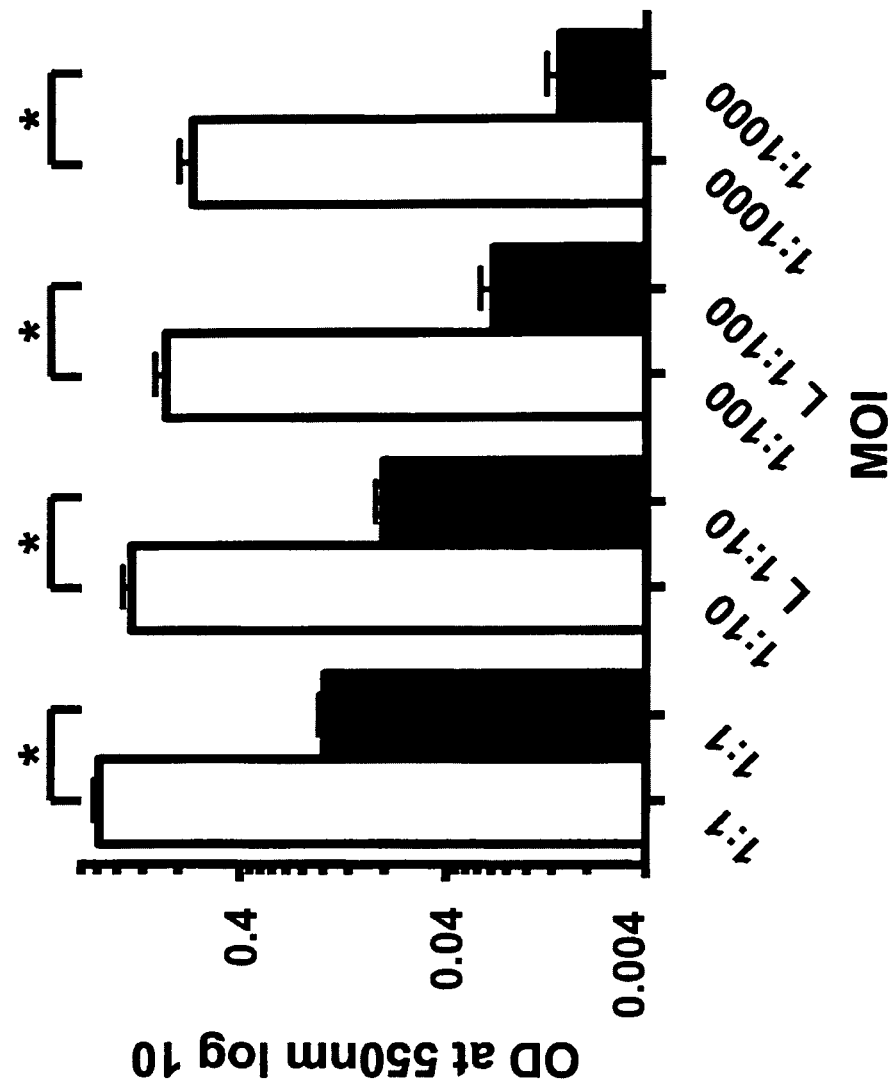
Figure 2D:
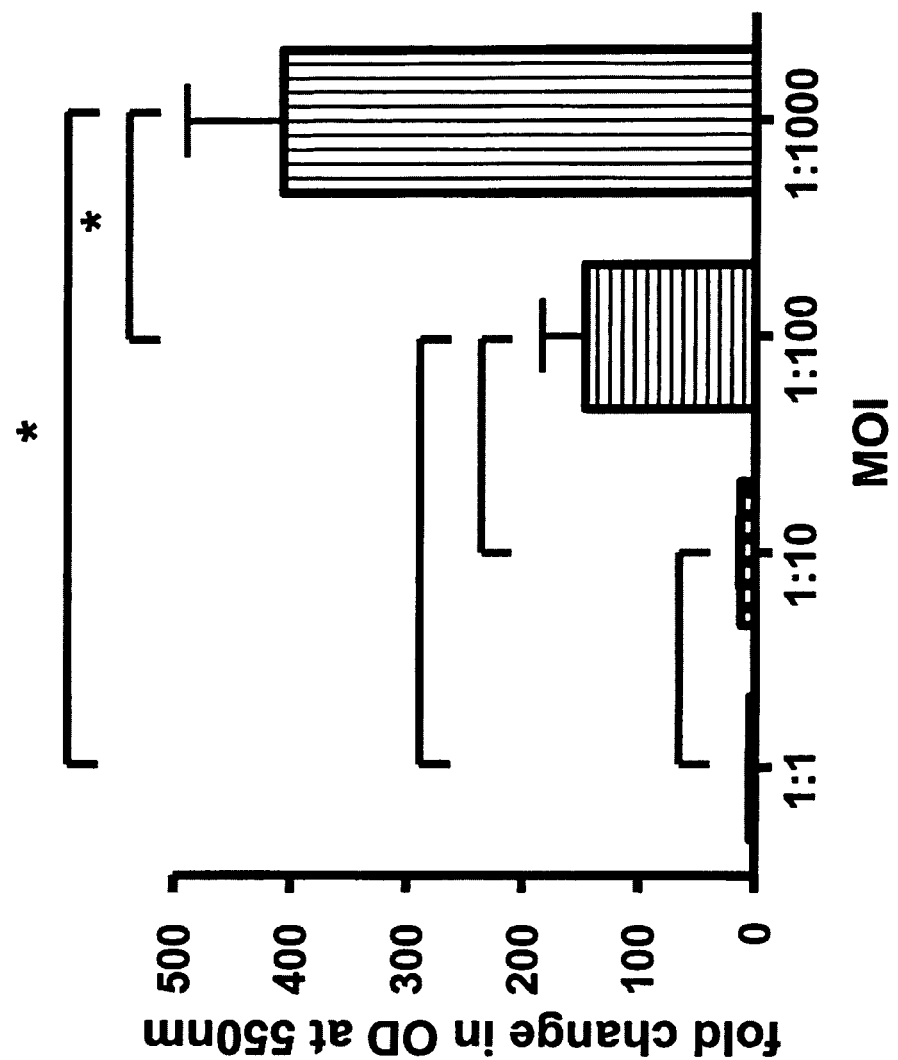
Figure 2E:
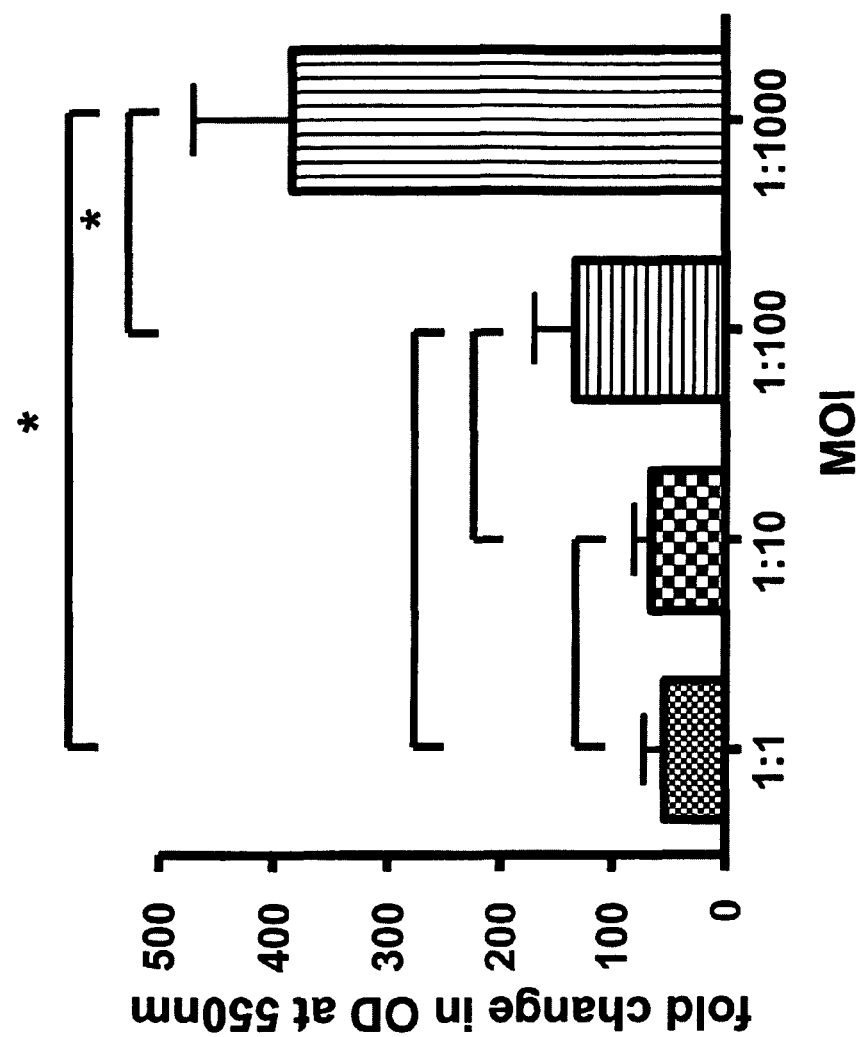

The addition of human neutrophils at every concentration of all strains tested resulted in a significant increase of biofilm formation at 24 hours when compared to biofilms formed without human neutrophils, except for PAO1 at a 1:1 bacteria to neutrophil ratio (FIG. 2A) by repeated measures ANOVA followed by Tukey's post test which tests the significance of multiple data sets in multiple comparisons (FIG. 2A-C).

Figure 2F:
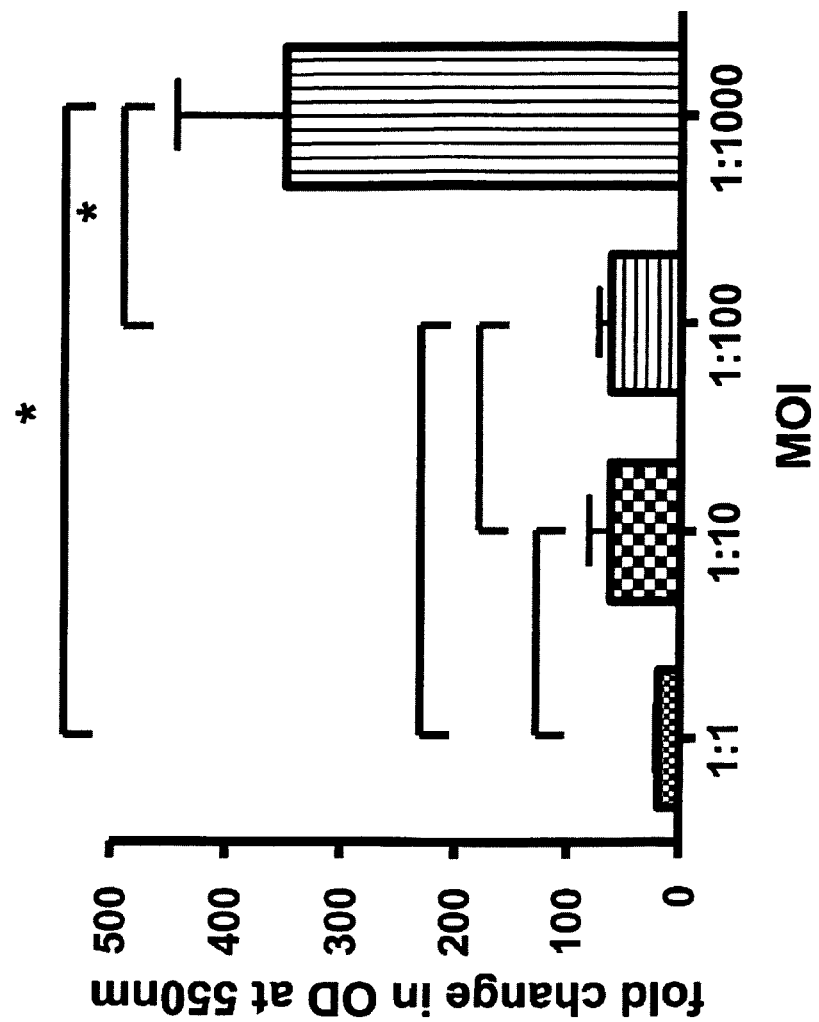

The relative induction effect resulting from the presence of the human neutrophil is depicted by the fold change in biofilm formation induced by the presence of neutrophils for PA01 (FIG. 2D), Early CF strain (FIG. 2E), and the late CF strain (FIG. 2F). Neutrophil induced biofilms of the Early, Late, and PAO1 strains showed a significant difference of biofilm density between concentration ratios of bacteria to neutrophils of 1:1 compared to 1:1000. The 1:1000 ratio also displayed a significant increase over the biofilm produced by the 1:100 ratio. Overall, all three strains followed similar patterns in uninduced and neutrophil-induced biofilm formation at 24 hours. Thus, tests of biofilm disruption (below) were conducted only with strain PA01.

Example 2

The following example can be used to demonstrate the association of charged polyamino acids with structures of early biofilms The action of the polyanionic peptide is thought to sequester the positively charged histone from this otherwise negatively charged complex of DNA and F-actin, resulting in biofilm dissolution.

To illustrate the association between histones and the test peptides, the amino acids can be biotinylated (Pierce biosciences, Rockford, Ill., cat #21335), combined with H1 histones (Calbiochem, San Diego, Calif.). The complex can then be extracted by the immunoprecipitation of the histone, and run on a western. The presence of both on a western blot would demonstrate the relationship and interaction between these elements.

Example 3

The following example demonstrates that *Pseudomonas* PAO1 biofilms induced by neutrophils are sensitive to charged amino acid chains.

Approximately 75 mer polyamino acids were added to a 24 hour neutrophil induced *P. aeruginosa* biofilm for a period of 3 hours at 37° C. when the biofilms were removed from the presence of neutrophil products and treated in saline. As shown in FIG. 3A, both concentrations of poly(D) (negative charge) exhibited a significant disruption of the biofilm relative to the untreated control, and 10 μm polyamino acids (black) had a greater disruption effect in saline than the 5 μm concentration (white) as measured by optical density from crystal violet staining. Both concentrations of poly(R) (positive charge) also exhibited a significant disruption of the biofilm relative to the untreated control, and 10 μm polyamino acids (black) trended towards a greater disruption effect than the 5 μm concentration (white) as measured by optical density from crystal violet staining. Neutral poly(S) displayed no effect. Significance (*) was calculated by one way ANOVA followed by Dunnetts' post test at $p<0.05$ and (**) t-test $p<0.05$.

Example 4

The following example demonstrates that *Pseudomonas* PAO1 biofilms induced by neutrophils are sensitive to charged amino acid chains of different lengths.

Approximately 75 mer polyamino acid (open bars) or approximately 260 mer polyamino acid chains (striped bars) were added to a 24 hour neutrophil induced *P. aeruginosa* biofilm for a period of 3 hours at 37° C. when the biofilms were removed from the presence of neutrophils products and treated in saline. As shown in FIG. 3B, poly(D) (negative charge), and poly(R) in the longer form exhibited greater disruption of the biofilm than their respective shorter chain form as measured by optical density from crystal violet staining. Significance (*) was calculated by one way ANOVA followed by Dunnetts' post test at $p<0.05$ and (**) t-test $p<0.05$.

Example 5

The following example demonstrates that *Pseudomonas* PAO1 biofilms induced by neutrophils are sensitive to charged amino acid chains without the removal of the neutrophils present during biofilm formation.

Approximately 75 mer polyamino acids were added to a 24 hour neutrophil induced *P. aeruginosa* biofilm for a period of 3 hours at 37° C. without removal of the neutrophils present during biofilm formation. As shown in FIG. 3C, poly(D) (negative charge) failed to disrupt the biofilm in either concentrations of 5 uM or 10 uM, and poly(R) exhibited a dose dependent response, where 10 μm poly(amino) acids (black) had a significantly greater disruption effect in saline than the 5 μm concentration (white) as measured by optical density from crystal violet staining. Neutral poly(S) displayed no effect. Significance (*) was calculated by one way ANOVA followed by Dunnetts' post test at $p<0.05$ and (**) t-test $p<0.05$.

Example 6

The following example shows that *Pseudomonas* PAO1 biofilms induced by neutrophils are sensitive to charged amino acid chains of different lengths without the removal of the neutrophils present during biofilm formation.

Approximately 75 mer polyamino acid (open bars) or approximately 260 mer polyamino acid chains (striped bars) were added to a 24 hour neutrophil induced *P. aeruginosa*) for a period of 3 hours at 37° C. without removal of the neutrophils present during biofilm formation. As shown in FIG. 3D, poly(R) exhibited a dose dependent response, where the long chain form had a greater disruption effect in saline than the short chain as measured by optical density from crystal violet staining. Significance (*) was calculated by one way ANOVA followed by Dunnetts' post test at $p<0.05$ and (**) t-test $p<0.05$.

Example 7

The following example shows the effect of protease inhibitors on polyamino acid disruption of neutrophil induced *P. aeruginosa* biofilms with and without the removal of the neutrophils present during biofilm formation.

Long chain (~260 mer, 5 μM) polyaspartic acid and polyarginine were used to treat a 24 hour neutrophil induced *P. aeruginosa* biofilm in the presence (black bars) or absence (open bars) of a protease inhibitor cocktail containing Aprotinin, Leupeptin, and Pepstatin A. As shown in FIG. 4A, when the biofilms were removed from the presence of neutrophil products and treated in saline, both Poly(D) and poly(R) exhibited a disruptive effect, with no enhancement induced by the protease inhibitor cocktail. As shown in FIG. 4B, when the neutrophils and neutrophil products in which the biofilm developed are present, poly(D) achieved significant disruption of the biofilm in the presence of the protease inhibitor cocktail. Significance (*) was calculated by one-way ANOVA followed by Dunnetts' post test at $p<0.05$ and (**) t-test $p<0.05$.

Example 8

The following example shows that neutrophil induced *P. aeruginosa* biofilms are disrupted by DNase.

*P. aeruginosa* PAO1 biofilms ($2.5 \times 10^3$ CFU) grown for 24 hours in the presence of neutrophils ($2.5 \times 10^6$ for a 1:1000 ratio) were treated with DNase for 3 hours, with biofilm disruption measured by crystal violet optical density. As shown in FIG. 5, DNase induced significant disruption of the biofilm while RNase had no effect, supporting the concept that DNA is also an important component in early neutrophil-induced biofilm development. Significance (*) was calculated by one-way ANOVA followed by Dunnetts' post test at p<0.05.

Example 9

The following example demonstrates that clinical levels of antibiotics alone do not disrupt biofilms.

Currently, the only recognized treatment for *P. aeruginosa* are antibiotics, such as ciprofloxacin or tobramycin. In order to establish the relative effectiveness of polypeptides or DNase in dispersing *P. aeruginosa* biofilm, we tested the ability of clinically relevant antibiotics to disrupt a biofilm induced by human neutrophils. *P. aeruginosa* biofilms (24-hour-old) were exposed to 2-fold dilutions of either ciprofloxacin or tobramycin over a clinically relevant range from 1024 ug/mL to 8 ug/mL. The biofilms were exposed for 3 hours to antibiotics, then quantified by crystal violet staining as described above. Even under high concentration, the antibiotics demonstrated no capacity to disrupt the *P. aeruginosa* biofilm (FIG. 6).

Example 10

The following example demonstrates the effect of charged amino acid chains in preventing neutrophil-induced enhancement of *P. aeruginosa* biofilms.

Approximately 75 mer polyamino acid chains of Asp, Arg and Ser at 10 uM were added at time=0 to *P. aeruginosa* PAO1 ($2.5 \times 10^3$ CFU) in the presence of neutrophils ($2.5 \times 10^6$ for a 1:1000 ratio). Following 24 hours at 37° C., the capacity of these products to modify biofilm development was tested by crystal violet staining. As shown in FIG. 7, both Poly(D) and Poly(R) prevented biofilm formation, with polyR better then polyD. Neutral polyS hand no effect. Significance (*) was calculated by one way ANOVA followed by Dunnetts' post test at p<0.05 and (**) t-test p<0.05.

Example 11

The following example demonstrates the effect of protease inhibitors in combination with charged amino acid chains in preventing neutrophil-induced enhancement of *P. aeruginosa* biofilms.

Approximately 75 mer polyamino acid chains of Asp, Arg and Ser at 10 uM were added at time=0 to *P. aeruginosa* PAO1 ($2.5 \times 10^3$ CFU) in the presence of neutrophils ($2.5 \times 10^6$ for a 1:1000 ratio) and in the presence (black bar) or absence (white bar) of a protease inhibitor cocktail. Following 24 hours at 37° C., the capacity of these treatments to modify biofilm development was tested by crystal violet staining. As shown in FIG. 8, the addition of protease inhibitors did not significantly enhance the capacity of polyD or polyR to prevent biofilm formation under the conditions tested. Significance (*) was calculated by one way ANOVA followed by Dunnetts' post test at p<0.05 and (**) t-test p<0.05.

Example 12

The following example demonstrates that neutrophil induced *P. aeruginosa* biofilm formation is prevented by DNase.

*P. aeruginosa* PAO1 biofilms ($2.5 \times 10^3$ CFU) grown for 24 hours in the presence of neutrophils ($2.5 \times 10^6$ for a 1:1000 ratio) in the presence of DNase or RNase. Following 24 hours at 37° C., the capacity of these treatments to modify biofilm development was tested by crystal violet staining. As shown in FIG. 9, while DNase significantly prevented the formation of the biofilm, RNase had no effect. Significance (*) was calculated by one-way ANOVA followed by Dunnetts' post test at p<0.05.

Although treatment of established *P. aeruginosa* biofilms is currently the most relevant clinical scenario, under certain situations, biofilm formation is a highly predictable event. If agents existed that were effective in preventing the formation of the biofilm, alternative strategies could be employed to reduce the potential for biofilm formation. We tested the capacity of poly(D) or poly(R) to inhibit biofilm development when added directly to a mixture of *P. aeruginosa* and neutrophils. Biofilm development was quantified after 24 hours incubation as detailed above. Poly(R) was more effective at preventing the formation of biofilms, even in the absence of a protease inhibitor. DNase also significantly prevented biofilm formation under these conditions (not shown).

The robust activity of poly(R) in the prevention of biofilm formation led to a question of an alternate mechanism of disruption in this system. To address this, the antibiotic potential of all the components of the peptide assays were tested individually and, when appropriate, in combination. We found that within assays, the amount of bacteria recovered from pooled wells was consistent, and that poly(R) in every concentration tested was bactericidal or bacteriostatic (not shown). The protease inhibitors pepstatin A, leupeptin, and aprotinin alone or in combination displayed no toxicity. The uncharged poly(S) as well as the negatively charged poly(D) likewise had no intrinsic antibiotic effect alone or when combined with the abovementioned protease inhibitor triad. These data may help to explain why poly(R) was so effective in the prevention of biofilm formation; likely the peptide can both directly kill *P. aeruginosa* in addition to disrupting the biofilm.

Example 13

The following example demonstrates that neutrophils significantly enhance early *Burkholderia* biofilm development.

As with *P. aeruginosa*, various *Burkholderia* species, with relatively little potential to form biofilms in vitro, achieve enhanced biofilm formation to varying degrees when exposed to human neutrophils. *Burkholderia* biofilms ($2.5\times10^3$ CFU) were grown for 24 hours in the presence of neutrophils ($2.5\times10^6$ for a 1:1000 ratio). As shown in FIG. 10, the largest response was seen by *B. thailandensis*, which at 24 hours demonstrated a greater then 180-fold increase in biofilm development induced by the addition of neutrophils, when compared to biofilm development in the absence of neutrophils.

Example 14

The following example demonstrates the dispersion of early *Burkholderia* biofilms by anionic polyamino acids of different lengths.

Approximately 75 mer polyamino or approximately 260 mer polyamino acid chains (Asp, Arg or Ser) were added to a 24 hour neutrophil induced *B. Thailandensis* biofilm for a period of 3 hours at 37° C., when the biofilms were removed from the presence of neutrophil products and treated in saline. As shown in FIG. 11, 260 mer poly(D) induced disruption of the biofilm as measured by optical density from crystal violet staining. Significance (*) was calculated by one-way ANOVA followed by Dunnetts' post test at p<0.05.

Example 15

The following example demonstrates that *Pseudomonas aeruginosa* biofilm density is increased by the presence of human neutrophils.

Human neutrophils isolated from healthy volunteers were combined with *P. aeruginosa* strain PA01 (FIG. 12A), an Early CF isolate (FIG. 12B), and an isogenic Late CF isolate (FIG. 12C) over a range of bacteria to neutrophil ratios spanning 4-logs. All ratios of bacteria to neutrophils tested resulted in a significant (p<0.05) enhancement of biofilm density when compared to *P. aeruginosa* of equal concentration grown in the absence of neutrophils, as measured by crystal violet staining.

In the absence of neutrophils, decreasing initial concentrations of bacteria (inocula ranging from $2.5 \times 10^6$ to $2.5 \times 10^3$ CFU) resulted in a decrease in biofilm density from each concentration to the next, save the two most dilute samples by one-way ANOVA followed by Tukey's post test. Under the conditions tested, a basal level of biofilm formation is reached at an inoculum of $2.5 \times 10^4$.

The addition of human neutrophils at every concentration of all strains tested resulted in a significant increase of biofilm formation at 24 hours when compared to biofilms formed without human neutrophils (FIG. 12A-C), except for PAO1 at a 1:1 bacteria to neutrophil ratio (FIG. 12A).

The relative induction effect resulting from the presence of the human neutrophil is depicted by the fold change in biofilm formation induced by the presence of neutrophils for PA01 (FIG. 12D), Early CF strain (FIG. 12E), and the Late CF strain (FIG. 12F). Neutrophil induced biofilms of the Early, Late, and PAO1 strains showed a significant increase of biofilm density between concentration ratios of bacteria to neutrophils of 1:1 compared to 1:0.001. The 1:0.001 ratio also displayed a significant increase over the biofilm produced by the 1:0.01 ratio.

Biofilms of *P. aeruginosa* strain PAO1 (FIGS. 13 and 20) as well as the Early and Late CF strains (FIGS. 21 and 22) were formed by combining $2.5 \times 10^4$ CFU with $2.5 \times 10^6$ neutrophils (PMN to bacteria ratio of 1:0.01) over 48 hours, and compared by scanning electron microscopy (SEM) to biofilms grown in the absence of neutrophils. The presence of neutrophils evoked clear differences that were evident by SEM. Neutrophil-induced biofilms largely covered each peg, where in the absence of neutrophils, only scattered aggregates of bacteria were visualized (FIGS. 13 and 20-22). In addition, the architecture of the biofilm was dramatically thicker and more developed in the presence of neutrophils. Generally, all three strains followed similar patterns in uninduced and neutrophil-induced biofilm formation at 48 hours.

Example 16

The following example demonstrates the disruption of neutrophil induced *P. aeruginosa* biofilms by both anionic and cationic polyaminno acids.

Three peptides of equivalent length (median length of 74 mer) were compared for their capacity to disrupt a 24-hour-old biofilm of *P. aeruginosa* formed in the presence of human neutrophils (1:0.001 ratio). Homopeptides chains of anionic (Asp)$_{74}$, cationic (Arg)$_{74}$, and a polar but uncharged (Ser)$_{74}$ were analyzed. When the 24-hour biofilms were combined with these poly(amino acids) suspended in saline (free of neutrophil products not incorporated in the biofilm) for 3 hours, a significant concentration related disruption of biofilms was present in response to (Asp)$_{74}$ (FIG. 14A). Unexpectedly, (Arg)$_{74}$ also had a significant effect in disrupting biofilms, likely by an alternate charge related mechanism. The effect of the anionic peptide is dose related, as there was a significant decrease in biofilm density as the concentration of (Asp)$_{74}$ was increased from 5 µm to 10 µm (FIG. 14A). The polar but uncharged (Ser)$_{74}$ did not cause disruption of the biofilm at either 5 µm and 10 µm concentrations (FIG. 14A).

Example 17

The following example demonstrates the effect of polyamino acid chain length on biofilm disruption.

To establish whether or not the biofilm disrupting effect of positively and/or negatively charged peptides is related to the length of the polymer chain, we compared the effect of longer charged polypeptides. Using equimolar concentrations, amino acid chains of 260 residues were compared to the 74-mer polypeptides to determine the effect of chain length on biofilm disruption. Under these conditions, (Asp)$_{260}$ was more effective than (Asp)$_{74}$, and (Arg)$_{260}$ had a greater effect than (Asp)$_{74}$ (FIG. 14B).

Example 18

The following example demonstrates that proteases reduce the capacity of charged poly(amino acids) to disrupt neutrophil induced *P. aeruginosa* biofilms.

When poly(amino acids) were added directly to the milieu of neutrophil lysate in which the biofilm was formed, the capacity of poly(amino acids) to disrupt biofilms was diminished (FIG. 15A) compared to reactions conducted in saline (FIG. 14). Under these conditions, only (Arg)$_{74}$ was capable of a reduction in the density of biofilms following a 3 hour exposure, with a slightly greater effect exhibited when the amino acid concentration was doubled from 5 µm (white bars) to 10 µm (black bars) (FIG. 15A). Similarly, when the long chain and short chain poly(amino) acids were compared, (Arg)$_{74}$ had a small effect, becoming more effective with increased chain length (FIG. 15B). As both neutrophils and *P. aeruginosa* contain and/or synthesize an array of proteases, which degrade peptide chains, we tested the capacity of a protease inhibitor cocktail to enhance the potential of poly(amino acids) to disrupt the biofilm under these conditions. In the presence of protease inhibitors, (Asp)$_{260}$ significantly disrupted the biofilm compared to the untreated control (FIG. 15C; the right three bars are without (Asp)$_{260}$, the left three bars are with (Asp)$_{260}$, with the first bar of each group of three representing no protease inhibitors, the second 1× protease inhibitors, and the third 7× protease inhibitors). With a 7-fold greater concentration of protease inhibitors, there is an even greater restoration of the ability of (Asp)$_{260}$ to disrupt biofilms, increased from 25% to 52% reduction in biofilm density (FIG. 15C). When the biofilms were removed from the overnight culture material containing the products of necrotic neutrophils (such as proteases of bacterial and neutrophil origin), and washed once in saline, addition of either (Asp)$_{260}$ or (Arg)$_{260}$ exhibited a significant disruptive effect, with no additional enhancement achieved by the addition of the protease inhibitor cocktail (FIG. 15D). These data support the conclusion that an anionic polypeptide can disrupt *P. aeruginosa* biofilms formed in the presence of human neutrophils, but proteolytic degradation, likely mediated by both bacteria and neutrophils can reduce the effectiveness of poly(amino acids) in a neutrophil-rich environment.

Example 19

The following example demonstrates that antibiotics are incapable of disrupting neutrophil-induced biofilms.

Currently, the only recognized treatment for *P. aeruginosa* is antibiotics such as ciprofloxacin or tobramycin, although treatment with DNase has also been associated with decreased *Pseudomonas aeruginosa* infection in the CF airway. In order to compare the relative effectiveness of polypeptides in dispersing *P. aeruginosa* biofilm in this system, we tested the ability of clinically-relevant antibiotics to disrupt a biofilm induced by human neutrophils. *P. aeruginosa* biofilms (24-hour-old) were exposed to 2-fold dilutions of either ciprofloxacin (FIG. 16A) or tobramycin (FIG. 16B) in a clinically relevant concentrations ranging from 8 ug/mL to 1024 ug/mL. The biofilms were exposed for 3 hours to antibiotics then quantified as described above with crystal violet. Even under the highest concentration, the antibiotics demonstrated no capacity to disrupt the neutrophil-induced *P. aeruginosa* biofilm (FIG. 16), consistant with the well-established principle that biofilm formation induces a resistance to antibiotics.

Example 20

The following example demonstrates the capacity of poly (amino acid) chains to prevent *P. aeruginosa* biofilm formation.

Although treatment of established *P. aeruginosa* biofilms likely represents the most relevant clinical scenario, in certain situations, biofilm formation is a highly predictable event. If agents existed that were effective in preventing the formation of the biofilm, alternative strategies could be employed to reduce the potential for biofilm formation. We tested the capacity of $(Asp)_{74}$, $(Arg)_{74}$, or $(Ser)_{74}$ to inhibit biofilm development when added directly to a mixture of *P. aeruginosa* and neutrophils (FIG. 17). Biofilm development was quantified after 24 hours incubation as detailed above. While $(Asp)_{74}$ was effective at preventing the formation of biofilms, it was less effective then $(Arg)_{74}$. Uncharged $(Ser)_{74}$ demonstrated no capacity to prevent biofilm formation.

The unexpectedly robust activity of $(Arg)_{74}$ in the prevention of biofilm formation led to a question of an alternate mechanism of disruption in this system. To address this, the antibiotic potential of all the components used in the peptide assays were tested individually and, when appropriate, in combination. We found that within assays, the amount of bacteria recovered from pooled wells was consistent, and that $(Arg)_{74}$ in every concentration tested was bactericidal (not shown). The protease inhibitors pepstatin A, leupeptin, and aprotinin alone or in combination displayed no antimicrobial effect. The uncharged $(Ser)_{74}$, as well as the negatively charged $(Asp)_{74}$, had no intrinsic antibiotic effect alone or when combined with the protease inhibitor triad. This data may help to explain why $(Arg)_{74}$ was especially effective in the prevention of biofilm formation; likely the peptide can both directly kill *P. aeruginosa* in addition to disrupting the biofilm. While highly cationic proteins can serve as antimicrobials, we are not aware of previous reports of simple poly(amino acids) with this property.

Example 21

The following example demonstrates that DNase disrupts *P. aeruginosa* biofilms, and prevents their formation in the presence of neutrophils.

Previously, our group and others have shown the capacity of DNase to disrupt *P. aeruginosa* biofilms. Under the conditions used in Example 16 above, exposure to DNase for 3 hours disrupts 24-hour old neutrophil-induced biofilms (FIG. 18A). Likewise, DNase was able to significantly prevent biofilm formation in the presence of neutrophils (FIG. 18B), under the conditions described for Example 20. As expected, RNase demonstrated no capacity to disrupt (FIG. 18A) or prevent biofilm formation (FIG. 18B).

Example 22

The following example demonstrates that poly(aspartic acid) works in conjunction with DNase to disrupt biofilms.

While concentrated DNase (FIG. 18A) or poly(aspartic acid) (FIG. 14) are both capable of disrupting an early biofilm over the course of a 3 hour exposure, during DNase therapy in the CF airway it is likely that biofilms are exposed to DNase over a wide range of concentrations, and the effective duration of exposure may be quite brief. Furthermore, in the setting of chronic infections, biofilms are likely greater than 24 hours old. We tested the capacity of DNase and $(Asp)_{260}$ to disrupt biofilms when administered over a much shorter period, at lower concentrations, and with thicker and more mature biofilms.

When the duration of exposure to DNase was reduced to only 10 minutes, a 24 hour old neutrophil-induced biofilm at was still reduced by 75% (FIG. 19A). However, a biofilm grown for 48 hours was reduced by only 42% by 10 minutes of DNase treatment (FIG. 19B). Likewise, biofilms at later stages of growth (48 hours) also had greater resistance to disruption with $(Asp)_{260}$, either alone or in combination with DNase. Exposing a 24-hour neutrophil induced biofilm for only 10 minutes to $(Asp)_{260}$ resulted in a 49% reduction in biofilm density (FIG. 19A). When DNase was used in combination with $(Asp)_{260}$, the mixture resulted in an 82% reduction (FIG. 19A). Neither $(Asp)_{260}$ nor $(Arg)_{260}$ alone reduced the density of a thicker 48-hour biofilm (FIG. 19B), but when $(Asp)_{260}$ was used in conjunction with DNase, $(Asp)_{260}$ was able to reduce the biofilm by 78%, (FIG. 19B). In contrast, $(Arg)_{260}$ was unable to disrupt a 24-hour old biofilms when exposed for only 10 minutes (FIG. 19A), and when combined with DNase substantially reduced the capacity of DNase to disrupt the 24 or 48 hour biofilm when compared to DNase alone (FIGS. 19A-B).

The combined effect of $(Asp)_{260}$ with DNase was dose-dependent (FIG. 19C). By decreasing DNase concentration four-fold (8.25 ug/ml), only a 16% decrease in the biofilm density of a 48 hour biofilm was achieved after 10 minutes treatment (FIG. 19C), compared to 42% at the 33 µg/mL dose (FIG. 19B). When the lower concentration of DNase was used in combination with $(Asp)_{260}$, the density of the biofilm was reduced by 67% (FIG. 19C), demonstrating the strongest synergistic effect between the enzyme and poly(aspartic acid). Thus, under conditions in which DNase as a single agent has little effect, the presence of $(Asp)_{260}$ significantly enhances the capacity of DNase to disrupt a biofilm formed in the presence of neutrophils.

Parallel experiments were conducted with the Early and Late CF strains. Neutrophil-induced biofilms of the Early CF strain (24 hour of growth) were not disrupted by a 10 min exposure to DNase (FIG. 23A), while the Late CF strain demonstrated a modest disruption (FIG. 23C). But for both strains, the effect of DNase was significantly increased by the addition of $(Asp)_{260}$ (FIGS. 23A and C). The additive effect of DNase and $(Asp)_{260}$ was also apparent following 48-hours of biofilm growth for both the early and late CF strains (FIGS.

23B and D). Perhaps of greatest clinical interest are attempts to disrupt the mucoid late CF strain that had been allowed to form for 48-hours in the presence of neutrophils (FIG. 23D). Under these conditions, only the combination of DNase and (Asp)$_{260}$ achieved disruption of the biofilm (FIG. 23D).

Each publication cited herein is incorporated herein by reference in its entirety.

REFERENCES

1. Khan, T. Z., Wagener, J. S., Bost, T., Martinez, J., Accurso, F. J., and Riches, D. W. 1995. Early pulmonary inflammation in infants with cystic fibrosis. *Am J Respir Crit Care Med* 151:1075-1082.
2. Muhlebach, M. S., and Noah, T. L. 2002. Endotoxin activity and inflammatory markers in the airways of young patients with cystic fibrosis. *Am J Respir Crit Care Med* 165:911-915.
3. Muhlebach, M. S., Stewart, P. W., Leigh, M. W., and Noah, T. L. 1999. Quantitation of inflammatory responses to bacteria in young cystic fibrosis and control patients. *Am J Respir Crit Care Med* 160:186-191.
4. Burns, J. L., Gibson, R. L., McNamara, S., Yim, D., Emerson, J., Rosenfeld, M., Hiatt, P., McCoy, K., Castile, R., Smith, A. L., et al. 2001. Longitudinal assessment of Pseudomonas aeruginosa in young children with cystic fibrosis. *J Infect Dis* 183:444-452.
5. Frederiksen, B., Lanng, S., Koch, C., and Hoiby, N. 1996. Improved survival in the Danish center-treated cystic fibrosis patients: results of aggressive treatment. *Pediatr Pulmonol* 21:153-158.
6. Rosenfeld, M., Gibson, R. L., McNamara, S., Emerson, J., Burns, J. L., Castile, R., Hiatt, P., McCoy, K., Wilson, C. B., Inglis, A., et al. 2001. Early pulmonary infection, inflammation, and clinical outcomes in infants with cystic fibrosis. *Pediatr Pulmonol* 32:356-366.
7. Emerson, J., Rosenfeld, M., McNamara, S., Ramsey, B., and Gibson, R. L. 2002. Pseudomonas aeruginosa and other predictors of mortality and morbidity in young children with cystic fibrosis. *Pediatr Pulmonol* 34:91-100.
8. Parad, R. B., Gerard, C. J., Zurakowski, D., Nichols, D. P., and Pier, G. B. 1999. Pulmonary outcome in cystic fibrosis is influenced primarily by mucoid Pseudomonas aeruginosa infection and immune status and only modestly by genotype. *Infect Immun* 67:4744-4750.
9. Schaedel, C., de Monestrol, I., Hjelte, L., Johannesson, M., Komfalt, R., Lindblad, A., Strandvik, B., Wahlgren, L., and Holmberg, L. 2002. Predictors of deterioration of lung function in cystic fibrosis. *Pediatr Pulmonol* 33:483-491.
10. Drenkard, E., and Ausubel, F. M. 2002. Pseudomonas biofilm formation and antibiotic resistance are linked to phenotypic variation. *Nature* 416:740-743.
11. Ernst, R. K., Yi, E. C., Guo, L., Lim, K. B., Burns, J. L., Hackett, M., and Miller, S. I. 1999. Specific lipopolysaccharide found in cystic fibrosis airway Pseudomonas aeruginosa. *Science* 286:1561-1565.
12. Spencer, D. H., Kas, A., Smith, E. E., Raymond, C. K., Sims, E. H., Hastings, M., Burns, J. L., Kaul, R., and Olson, M. V. 2003. Whole-genome sequence variation among multiple isolates of Pseudomonas aeruginosa. *J Bacteriol* 185:1316-1325.
13. Aaron, S. D., Ferris, W., Ramotar, K., Vandemheen, K., Chan, F., and Saginur, R. 2002. Single and combination antibiotic susceptibilities of planktonic, adherent, and biofilm-grown Pseudomonas aeruginosa isolates cultured from sputa of adults with cystic fibrosis. *J Clin Microbiol* 40:4172-4179.
14. Singh, P. K., Schaefer, A. L., Parsek, M. R., Moninger, T. O., Welsh, M. J., and Greenberg, E. P. 2000. Quorum-sensing signals indicate that cystic fibrosis lungs are infected with bacterial biofilms. *Nature* 407:762-764.
15. Klausen, M., Heydorn, A., Ragas, P., Lambertsen, L., Aaes-Jorgensen, A., Molin, S., and Tolker-Nielsen, T. 2003. Biofilm formation by Pseudomonas aeruginosa wild type, flagella and type IV pili mutants. *Mol Microbiol* 48:1511-1524.
16. Balfour-Lynn, I. M. 1999. The protease-antiprotease battle in the cystic fibrosis lung. *J R Soc Med* 92 Suppl 37:23-30.
17. Lethem, M. I., James, S. L., Marriott, C., and Burke, J. F. 1990. The origin of DNA associated with mucus glycoproteins in cystic fibrosis sputum. *Eur Respir J* 3:19-23.
18. Perks, B., and Shute, J. K. 2000. DNA and actin bind and inhibit interleukin-8 function in cystic fibrosis sputa: in vitro effects of mucolytics. *Am J Respir Crit Care Med* 162:1767-1772.
19. Roum, J. H., Buhl, R., McElvaney, N. G., Borok, Z., and Crystal, R. G. 1993. Systemic deficiency of glutathione in cystic fibrosis. *J Appl Physiol* 75:2419-2424.
20. Sheils, C. A., Kas, J., Travassos, W., Allen, P. G., Janmey, P. A., Wohl, M. E., and Stossel, T. P. 1996. Actin filaments mediate DNA fiber formation in chronic inflammatory airway disease. *Am J Pathol* 148:919-927.
21. Dakin, C. J., Numa, A. H., Wang, H., Morton, J. R., Vertzyas, C. C., and Henry, R. L. 2002. Inflammation, infection, and pulmonary function in infants and young children with cystic fibrosis. *Am J Respir Crit Care Med* 165:904-910.
22. Walker, T. S., Tomlin, K. L., Worthen, G. S., Poch, K. R., Lieber, J. G., Saavedra, M. T., Fessler, M. B., Malcolm, K. C., Vasil, M. L., and Nick, J. A. 2005. Enhanced Pseudomonas aeruginosa biofilm development mediated by human neutrophils. *Infect Immun* 73:3693-3701.
23. Halmerbauer, G., Arri, S., Schierl, M., Strauch, E., and Koller, D. Y. 2000. The relationship of eosinophil granule proteins to ions in the sputum of patients with cystic fibrosis. *Clin Exp Allergy* 30:1771-1776.
24. Olsson, I., Venge, P., Spitznagel, J. K., and Lehrer, R. I. 1977. Arginine-rich cationic proteins of human eosinophil granules: comparison of the constituents of eosinophilic and neutrophilic leukocytes. *Lab Invest* 36:493-500.
25. Tang, J. X., Wen, Q., Bennett, A., Kim, B., Sheils, C. A., Bucki, R., and Janmey, P. A. 2005. Anionic poly(amino acid)s dissolve F-actin and DNA bundles, enhance DNase activity, and reduce the viscosity of cystic fibrosis sputum. *Am J Physiol Lung Cell Mol Physiol* 289:L599-605.
26. Haslett, C., Guthrie, L. A., Kopaniak, M. M., Johnston, R. B., Jr., and Henson, P. M. 1985. Modulation of multiple neutrophil functions by preparative methods or trace concentrations of bacterial lipopolysaccharide. *Am J Pathol* 119:101-110.
27. Onteniente, L., Brisse, S., Tassios, P. T., and Vergnaud, G. 2003. Evaluation of the polymorphisms associated with tandem repeats for Pseudomonas aeruginosa strain typing. *J Clin Microbiol* 41:4991-4997.
28. Ogle, J. W., Janda, J. M., Woods, D. E., and Vasil, M. L. 1987. Characterization and use of a DNA probe as an epidemiological marker for Pseudomonas aeruginosa. *J Infect Dis* 155:119-126.
29. Whitchurch, C. B., Tolker-Nielsen, T., Ragas, P. C., and Mattick, J. S. 2002. Extracellular DNA required for bacterial biofilm formation. *Science* 295:1487.
30. Downey, G. P., Worthen, G. S., Henson, P. M., and Hyde, D. M. 1993. Neutrophil sequestration and migration in localized pulmonary inflammation. Capillary localization and migration across the interalveolar septum. *Am Rev Respir Dis* 147:168-176.
31. Worlitzsch, D., Tarran, R., Ulrich, M., Schwab, U., Cekici, A., Meyer, K. C., Birrer, P., Bellon, G., Berger, J., Weiss, T., et al. 2002. Effects of reduced mucus oxygen concentration in airway *Pseudomonas* infections of cystic fibrosis patients. *J Clin Invest* 109:317-325.
32. Yoon, S. S., Hennigan, R. F., Hilliard, G. M., Ochsner, U. A., Parvatiyar, K., Kamani, M. C., Allen, H. L., DeKievit, T. R., Gardner, P. R., Schwab, U., et al. 2002. *Pseudomonas aeruginosa* anaerobic respiration in biofilms: relationships to cystic fibrosis pathogenesis. *Dev Cell* 3:593-603.

While various embodiments of the present invention have been described in detail herein, it is apparent that modifications and adaptations of those embodiments will occur to those skilled in the art. It is to be expressly understood, however, that such modifications and adaptations are within the scope of the present invention, as set forth in the following claims:

We claim:

1. A method of treating or preventing bacterial keratitis in a subject, comprising administering a polyamino acid selected from the group consisting of polyaspartic acid and polyglutamic acid to a subject or treating a contact lens with a polyamino acid selected from the group consisting of polyaspartic acid and polyglutamic acid, wherein the polyamino acid inhibits or reduces neutrophil-induced biofilm formation associated with bacterial keratitis or associated with the contact lens.

2. The method of claim 1, wherein the polyamino acid is between 50 and 300 amino acids in length.

3. The method of claim 1, further comprising administering to the subject a protease inhibitor.

4. The method of claim 1, further comprising administering to the subject an anti-DNA compound.

5. The method of claim 1, further comprising administering to a subject a compound that inhibits accumulation of, inhibits necrosis of, or inhibits release of the cellular contents of, cells that undergo necrosis, at or proximal to the site of biofilm formation or the site of infection by a microorganism that forms biofilms.

6. The method of claim 5, wherein the cells that undergo necrosis are neutrophils.

7. The method of claim 6 wherein the compound inhibits the adherence of, migration to, or the sensing or response to chemoattractants by neutrophils, or inhibits the activity or release of a cytokine, chemokine or chemoattractant that attracts or enhances neutrophil activity.

8. The method of claim 7, wherein the compound is an anti-inflammatory compound.

9. The method of claim 5, further comprising administering to the subject an anti-DNA compound.

10. The method of claim 1, further comprising administering to the subject an anti-mucin compound.

11. The method of claim 1, wherein the compound is administered when bacterial keratitis is diagnosed or suspected.

12. The method of claim 1, wherein the compound is administered prior to the treatment of the subject with a process that may cause a biofilm to form in the patient.

13. The method of claim 1, wherein the compound is administered with a pharmaceutically acceptable carrier.

14. The method of claim 1, wherein the compound is administered directly to or proximal to the site of biofilm formation or potential therefore.

15. The method of claim 1, wherein the biofilm forms in connection with bacterial keratitis in an organ, tissue or body system.

16. The method of claim 1, wherein the biofilm forms on a surface of a tissue, organ or bodily part.

17. The method of claim 5, wherein the microorganism is *Pseudomonas aeruginosa.*

18. The method of claim 1, wherein the contact lens is disposable.

19. The method of claim 1, wherein the polyamino acid is synthetic polymer.

\* \* \* \* \*